US012594060B2

(12) United States Patent
Yamamoto

(10) Patent No.: US 12,594,060 B2
(45) Date of Patent: Apr. 7, 2026

(54) ULTRASOUND DIAGNOSTIC APPARATUS, CONTROL METHOD OF ULTRASOUND DIAGNOSTIC APPARATUS, AND PROCESSOR FOR ULTRASOUND DIAGNOSTIC APPARATUS

(71) Applicant: FUJIFILM Corporation, Tokyo (JP)

(72) Inventor: Katsuya Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 640 days.

(21) Appl. No.: 17/499,539

(22) Filed: Oct. 12, 2021

(65) Prior Publication Data

US 2022/0031288 A1 Feb. 3, 2022

Related U.S. Application Data

(63) Continuation of application No. PCT/JP2020/012945, filed on Mar. 24, 2020.

(30) Foreign Application Priority Data

Apr. 26, 2019 (JP) ................................. 2019-085841

(51) Int. Cl.
A61B 8/00 (2006.01)
A61B 8/06 (2006.01)
A61B 8/08 (2006.01)

(52) U.S. Cl.
CPC .................. *A61B 8/54* (2013.01); *A61B 8/06* (2013.01); *A61B 8/085* (2013.01); *A61B 8/463* (2013.01); *A61B 8/467* (2013.01); *A61B 8/488* (2013.01)

(58) Field of Classification Search
None
See application file for complete search history.

(56) References Cited

U.S. PATENT DOCUMENTS 6,322,509 B1 11/2001 Pan et al.
2001/0016686 A1* 8/2001 Okada .................. A61B 8/0858
600/454

(Continued)

FOREIGN PATENT DOCUMENTS

CN 107157515 A 9/2017
EP 0842638 A2 5/1998

(Continued)

OTHER PUBLICATIONS

An Office Action mailed by China National Intellectual Property Administration on Jun. 16, 2023, which corresponds to Chinese Patent Application No. 202080031227.6 and is related to U.S. Appl. No. 17/499,539; with English language translation.

(Continued)

*Primary Examiner* — Shahdeep Mohammed
(74) *Attorney, Agent, or Firm* — Studebaker Brackett PLLC

(57) ABSTRACT

An ultrasound diagnostic apparatus (1) includes a B-mode processing unit (6) that generates a B-mode image in which at least a blood vessel is imaged based on a reception signal obtained by transmitting and receiving ultrasonic waves to and from a subject; a display device (9) that displays the B-mode image; a vascular wall detection unit (10) that detects a vascular wall based on the B-mode image; a gate setting unit (11) that sets a Doppler gate in the blood vessel on the B-mode image; a Doppler processing unit (7) that acquires Doppler data in the Doppler gate; a blood flow velocity calculation unit (13) that calculates a blood flow velocity based on the Doppler data; and a blood flow rate measurement unit (12) that measures a blood flow rate based on the detected vascular wall and the calculated blood flow velocity, in which the blood flow rate is automatically measured based on a fixed start trigger.

13 Claims, 18 Drawing Sheets

(56) References Cited

U.S. PATENT DOCUMENTS

| | | | | |
|---|---|---|---|---|
| 2006/0184029 | A1* | 8/2006 | Haim | A61B 8/0833 |
| | | | | 600/443 |
| 2013/0281855 | A1* | 10/2013 | Baba | A61B 8/0883 |
| | | | | 600/441 |
| 2016/0270757 | A1* | 9/2016 | Toma | A61B 8/5223 |
| 2016/0302761 | A1* | 10/2016 | Lee | G16H 50/30 |
| 2017/0086780 | A1 | 3/2017 | Sokulin et al. | |
| 2017/0172538 | A1* | 6/2017 | Kristoffersen | A61B 8/06 |
| 2017/0193658 | A1* | 7/2017 | Cardinal | A61B 8/12 |
| 2018/0042578 | A1 | 2/2018 | Anand et al. | |
| 2019/0049567 | A1 | 2/2019 | Martins | |

FOREIGN PATENT DOCUMENTS

| | | | |
|---|---|---|---|
| EP | 1152364 | A2 | 11/2001 |
| JP | H02-152445 | A | 6/1990 |
| JP | H10-165400 | A | 6/1998 |
| JP | H10-216129 | A | 8/1998 |
| JP | 2002-052026 | A | 2/2002 |
| JP | 5384919 | B2 | 1/2014 |
| JP | 2018-529453 | A | 10/2018 |

OTHER PUBLICATIONS

The extended European search report issued by the European Patent Office on May 13, 2022, which corresponds to European Patent Application No. 20796184.8-1126 and is related to U.S. Appl. No. 17/499,539.

An Office Action mailed by China National Intellectual Property Administration on Jan. 2, 2024, which corresponds to Chinese Patent Application No. 202080031227.6 and is related to U.S. Appl. No. 17/499,539; with English language translation.

An Office Action; "Notice of Reasons for Refusal," mailed by the Japanese Patent Office on Nov. 1, 2022, which corresponds to Japanese Patent Application No. 2021-515885 and is related to U.S. Appl. No. 17/499,539; with English language translation.

International Search Report issued in PCT/JP2020/012945; mailed Jun. 9, 2020.

International Preliminary Report on Patentability and Written Opinion issued in PCT/JP2020/012945; issued Sep. 28, 2021.

Csurka et al.: Visual Categorization with Bags of Keypoints, Proc. of ECCV Workshop on Statistical Learning in Computer Vision, pp. 1-16 (2004).

Krizhevsk et al.: ImageNet Classification with Deep Convolutional Neural Networks, Advances in Neural Information Processing Systems 25, pp. 1-9 (2012).

Extended European Search Report issued in EP 24 19 7994.7-1122 by the European Patent Office on Oct. 30, 2024, which is related to U.S. Appl. No. 17/499,539.

An Office Action; mailed by the China National Intellectual Property Administration of the People's Republic of China on Nov. 5, 2024, which corresponds to Chinese Patent Application No. 202080031227.6 and is related to U.S. Appl. No. 17/499,539.

An Office Action; mailed by the China National Intellectual Property Administration of the People's Republic of China on Jan. 7, 2025, which corresponds to Chinese Patent Application No. 202080031227.6 and is related to U.S. Appl. No. 17/499,539.

* cited by examiner

RECEPTION CIRCUIT

4

23

24

25

AMPLIFICATION UNIT → AD CONVERSION UNIT → BEAM FORMER

B-MODE PROCESSING UNIT

6

26

27

28

SIGNAL PROCESSING UNIT → DSC → IMAGE PROCESSING UNIT

DOPPLER PROCESSING UNIT                                                    7

29                    30                    31                    32

| QUADRATURE DETECTION UNIT | HIGH-PASS FILTER | FAST FOURIER TRANSFORMER | DOPPLER WAVEFORM IMAGE GENERATION UNIT |

DATA MEMORY          33

FIG. 14

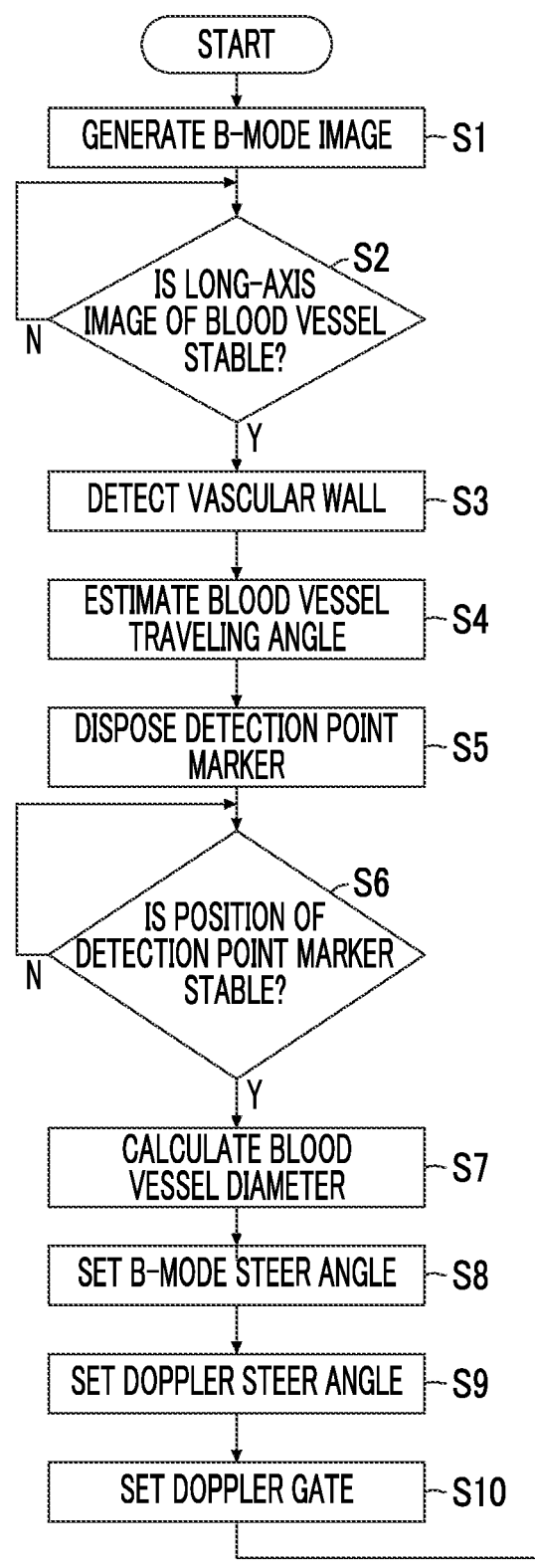

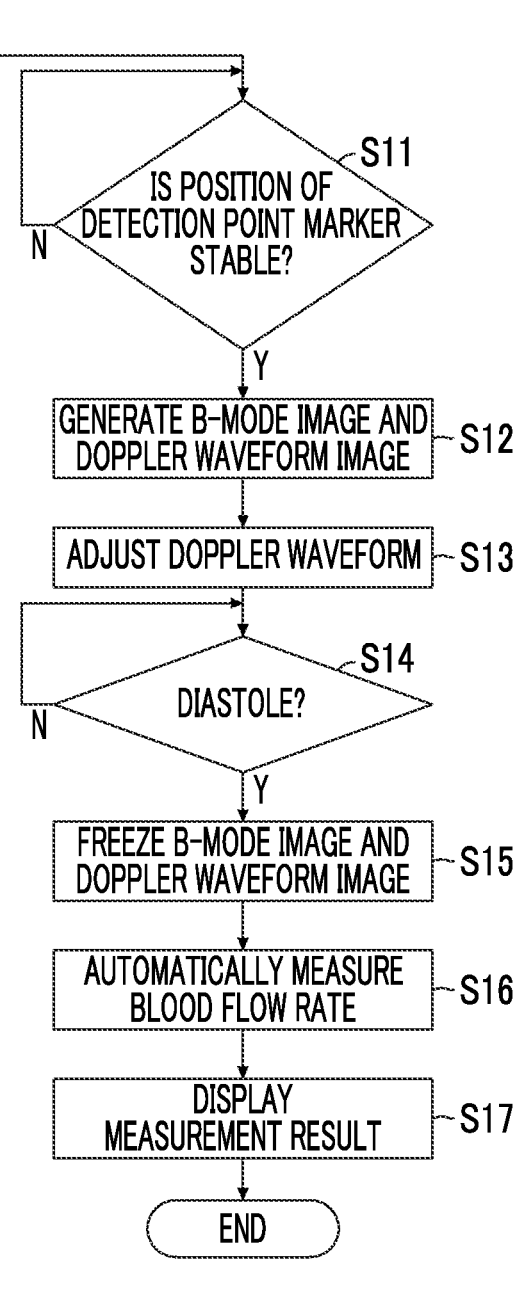

START

GENERATE B-MODE IMAGE — S1

IS LONG-AXIS IMAGE OF BLOOD VESSEL STABLE? — S2

N

Y

DETECT VASCULAR WALL — S3

ESTIMATE BLOOD VESSEL TRAVELING ANGLE — S4

DISPOSE DETECTION POINT MARKER — S5

IS POSITION OF DETECTION POINT MARKER STABLE? — S6

N

Y

CALCULATE BLOOD VESSEL DIAMETER — S7

SET B-MODE STEER ANGLE — S8

SET DOPPLER STEER ANGLE — S9

SET DOPPLER GATE — S10

IS POSITION OF DETECTION POINT MARKER STABLE? — S11

N

Y

GENERATE B-MODE IMAGE AND DOPPLER WAVEFORM IMAGE — S12

ADJUST DOPPLER WAVEFORM — S13

DIASTOLE? — S14

N

Y

FREEZE B-MODE IMAGE AND DOPPLER WAVEFORM IMAGE — S15

AUTOMATICALLY MEASURE BLOOD FLOW RATE — S16

DISPLAY MEASUREMENT RESULT — S17

END

MV2

BLOOD
FLOW RATE :
OO ml/min

UB

9

BLOOD FLOW
VELOCITY

UD

TIME

SL

9

BR

R1

UB

ULTRASOUND DIAGNOSTIC APPARATUS, CONTROL METHOD OF ULTRASOUND DIAGNOSTIC APPARATUS, AND PROCESSOR FOR ULTRASOUND DIAGNOSTIC APPARATUS

CROSS-REFERENCE TO RELATED APPLICATIONS

This application is a Continuation of PCT International Application No. PCT/JP2020/012945 filed on Mar. 24, 2020, which claims priority under 35 U.S.C. § 119(a) to Japanese Patent Application No. 2019-085841 filed on Apr. 26, 2019. The above application is hereby expressly incorporated by reference, in its entirety, into the present application.

BACKGROUND OF THE INVENTION

1. Field of the Invention

The present invention relates to an ultrasound diagnostic apparatus that acquires B-mode data and Doppler data, a control method of the ultrasound diagnostic apparatus, and a processor for the ultrasound diagnostic apparatus.

2. Description of the Related Art

In the related art, an ultrasound diagnostic apparatus has been known as an apparatus for obtaining an image of the inside of a subject. The ultrasound diagnostic apparatus generally comprises an ultrasound probe comprising a transducer array in which a plurality of elements are arranged. In a state where the ultrasound probe is in contact with a body surface of the subject, an ultrasound beam is transmitted toward the inside of the subject from the transducer array and an ultrasound echo from the subject is received by the transducer array so that element data is acquired. Further, the ultrasound diagnostic apparatus electrically processes the obtained element data to generate an ultrasound image of the corresponding site of the subject.

For example, JP2002-52026A discloses an ultrasound diagnostic apparatus which installs a Doppler gate on the B-mode image, sets a circular search region centered on a center point of the Doppler gate, and searches for B-mode intensity data outwards from the center along radial lines over an entire range of 360 degrees of the search region to detect a vascular wall.

SUMMARY OF THE INVENTION

However, for example, in a case where a blood flow rate is measured in the ultrasound diagnostic apparatus disclosed in JP2002-52026A, it is possible to measure a blood flow velocity using the Doppler gate, but it is necessary to separately measure a cross-sectional area of a blood vessel in addition to the measurement of the blood flow velocity and to calculate the blood flow rate on the basis of the measured cross-sectional area and blood flow velocity. In this way, in order to obtain a blood flow rate, a user has to perform an additional operation on the ultrasound diagnostic apparatus, which requires a great deal of time and effort.

The present invention has been made in order to solve such a problem in the related art, and an object of the present invention is to provide an ultrasound diagnostic apparatus, a control method of the ultrasound diagnostic apparatus, and a processor for the ultrasound diagnostic apparatus which can easily measure a blood flow rate.

In order to achieve the object, an ultrasound diagnostic apparatus according to an aspect of the present invention comprises a B-mode processing unit that generates a B-mode image in which at least a blood vessel is imaged based on a reception signal obtained by transmitting and receiving ultrasonic waves to and from a subject; a display device that displays the B-mode image; a vascular wall detection unit that detects a vascular wall by analyzing the B-mode image; a gate setting unit that sets a Doppler gate in the blood vessel on the B-mode image; a Doppler processing unit that acquires Doppler data in the Doppler gate; a blood flow velocity calculation unit that calculates a blood flow velocity based on the Doppler data; and a blood flow rate measurement unit that measures a blood flow rate based on the vascular wall detected by the vascular wall detection unit and the blood flow velocity calculated by the blood flow velocity calculation unit, in which the blood flow rate is automatically measured based on a fixed start trigger.

The vascular wall detection unit may set a search line for searching for the vascular wall on the B-mode image, and may detect an anterior vascular wall and a posterior vascular wall as the vascular wall based on a brightness profile of the B-mode image on the set search line.

It is preferable that the vascular wall detection unit sets a detection point marker on each of the detected anterior vascular wall and the detected posterior vascular wall, and causes the display device to display the detection point marker.

The gate setting unit may set the Doppler gate having a size and a center position decided based on coordinates of the anterior vascular wall and the posterior vascular wall detected by the vascular wall detection unit.

The vascular wall detection unit may search for the anterior vascular wall in a shallow direction and searches for the posterior vascular wall in a deep direction, at a plurality of positions separated in an orientation direction from a center position decided based on the coordinates of the anterior vascular wall and the posterior vascular wall detected by the vascular wall detection unit, estimate a blood vessel traveling angle, and set a Doppler steer angle such that an angle correction value for the blood vessel traveling angle is within 60 degrees.

The B-mode processing unit may generate the B-mode image based on a B-mode steer angle set according to the blood vessel traveling angle estimated by the vascular wall detection unit.

It is preferable that the vascular wall detection unit calculates a cross-sectional area of the blood vessel based on the detected vascular wall, and the blood flow rate measurement unit measures the blood flow rate by the product of the cross-sectional area calculated by the vascular wall detection unit and the blood flow velocity calculated by the blood flow velocity calculation unit.

It is preferable that the Doppler processing unit generates a Doppler waveform image based on the Doppler data, and the display device displays both the B-mode image generated by the B-mode processing unit and the Doppler waveform image generated by the Doppler processing unit.

The Doppler processing unit may generate the Doppler waveform image in parallel with the generation of the B-mode image by the B-mode processing unit, and the blood flow rate may be measured by the blood flow rate measurement unit with both the B-mode image and the Doppler waveform image being frozen.

Alternatively, the Doppler processing unit may acquire the Doppler data in the Doppler gate after the B-mode image is frozen, and generate the Doppler waveform image, and the blood flow rate may be measured by the blood flow rate measurement unit with the Doppler waveform image being frozen.

In the ultrasound diagnostic apparatus, the blood flow rate may be automatically measured with a fact that the blood vessel imaged in the B-mode image generated by the B-mode processing unit is changed from a short-axis image to a long-axis image as the start trigger.

In this case, in the ultrasound diagnostic apparatus, a time point at which an amount of change of a long-axis image of the blood vessel in the B-mode image is equal to or less than a fixed value may be used as the start trigger.

The ultrasound diagnostic apparatus may further comprise a microphone; and a voice recognition unit that recognizes a voice input through the microphone, in which the blood flow rate is automatically measured based on the start trigger given by the voice of a user.

A control method of an ultrasound diagnostic apparatus according to another aspect of the present invention comprises generating a B-mode image in which at least a blood vessel is imaged based on a reception signal obtained by transmitting and receiving ultrasonic waves to and from a subject; displaying the B-mode image; detecting a vascular wall by analyzing the B-mode image; setting a Doppler gate in the blood vessel on the B-mode image; acquiring Doppler data in the Doppler gate; calculating a blood flow velocity based on the Doppler data; and measuring a blood flow rate based on the detected vascular wall and the calculated blood flow velocity, in which the blood flow rate is automatically measured based on a fixed start trigger.

A processor for an ultrasound diagnostic apparatus according to still another aspect of the present invention is configured to generate a B-mode image in which at least a blood vessel is imaged based on a reception signal obtained by transmitting and receiving ultrasonic waves to and from a subject; display the B-mode image; detect a vascular wall by analyzing the B-mode image; set a Doppler gate in the blood vessel on the B-mode image; acquire Doppler data in the Doppler gate; calculate a blood flow velocity based on the Doppler data; and measure a blood flow rate based on the detected vascular wall and the calculated blood flow velocity, in which the blood flow rate is automatically measured based on a fixed start trigger.

According to the present invention, there are provided a B-mode processing unit that generates a B-mode image in which at least a blood vessel is imaged based on a reception signal obtained by transmitting and receiving ultrasonic waves to and from a subject; a display device that displays the B-mode image; a vascular wall detection unit that detects a vascular wall by analyzing the B-mode image; a gate setting unit that sets a Doppler gate in the blood vessel on the B-mode image; a Doppler processing unit that acquires Doppler data in the Doppler gate; a blood flow velocity calculation unit that calculates a blood flow velocity based on the Doppler data; and a blood flow rate measurement unit that measures a blood flow rate based on the vascular wall detected by the vascular wall detection unit and the blood flow velocity calculated by the blood flow velocity calculation unit, in which the blood flow rate is automatically measured based on a fixed start trigger. Therefore, it is possible to easily measure the blood flow rate.

BRIEF DESCRIPTION OF THE DRAWINGS

FIG. 14 is a flowchart illustrating an operation of the ultrasound diagnostic apparatus according to the first embodiment of the present invention.

DESCRIPTION OF THE PREFERRED
EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In addition, in the present specification, the terms "perpendicular" and "parallel" include a range of errors allowed in the technical field to which the present invention belongs. For example, the terms "perpendicular" and "parallel" mean a range less than ±10 degrees with respect to the strict perpendicular or parallel, and the error with respect to the strict perpendicular or parallel is preferably 5 degrees or less, and more preferably 3 degrees or less.

In the present specification, the terms "same" and "identical" include an error range generally allowed in the technical field. Further, in the present specification, in a case of referring to "all", "any", or "whole surface", the term includes an error range generally allowed in the technical field in addition to a case of 100%, and includes, for example, a case of 99% or more, a case of 95% or more, or a case of 90% or more.

First Embodiment

Figure 1:
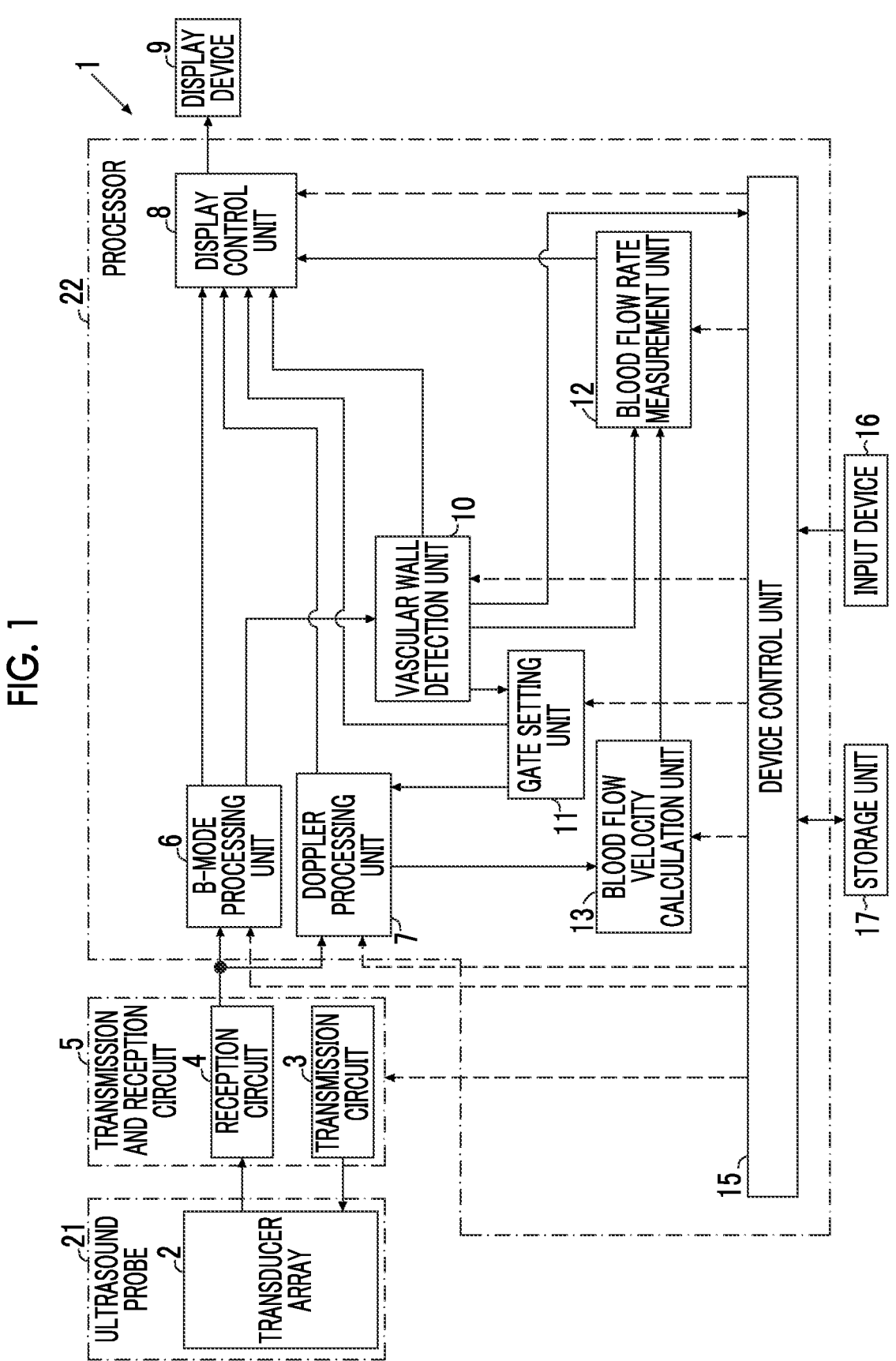
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. As illustrated in FIG. 1, the ultrasound diagnostic apparatus 1 comprises a transducer array 2, and each of a transmission circuit 3 and a reception circuit 4 is connected to the transducer array 2. Here, the transmission circuit 3 and the reception circuit 4 constitute a transmission and reception circuit 5. A Brightness mode (B-mode) processing unit 6 and a Doppler processing unit 7 are connected to the reception circuit 4, and a display device 9 is connected to the B-mode processing unit 6 and the Doppler processing unit 7 via a display control unit 8.

A vascular wall detection unit 10 is connected to the B-mode processing unit 6, and a gate setting unit 11 and a blood flow rate measurement unit 12 are connected to the vascular wall detection unit 10. The Doppler processing unit 7 is connected to the gate setting unit 11, and a blood flow velocity calculation unit 13 is connected to the Doppler processing unit 7. The blood flow rate measurement unit 12 is connected to the blood flow velocity calculation unit 13. The display control unit 8 is connected to the blood flow rate measurement unit 12.

In addition, a device control unit 15 is connected to the transmission and reception circuit 5, the B-mode processing unit 6, the Doppler processing unit 7, the display control unit 8, the vascular wall detection unit 10, the gate setting unit 11, the blood flow rate measurement unit 12, and the blood flow velocity calculation unit 13, and an input device 16 and a storage unit 17 are connected to the device control unit 15. The device control unit 15 and the storage unit 17 are connected so as to exchange information bidirectionally.

Further, the transducer array 2 is included in an ultrasound probe 21, and the B-mode processing unit 6, the Doppler processing unit 7, the display control unit 8, the vascular wall detection unit 10, the gate setting unit 11, the blood flow rate measurement unit 12, the blood flow velocity calculation unit 13, and the device control unit 15 constitute a processor 22 for the ultrasound diagnostic apparatus 1.

The transducer array 2 of the ultrasound probe 21 illustrated in FIG. 1 has a plurality of transducers arranged in a one-dimensional or two-dimensional manner. According to a drive signal supplied from the transmission circuit 3, each of the transducers transmits an ultrasonic wave and receives an ultrasound echo from a subject to output a signal based on the ultrasound echo. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission circuit 3 includes, for example, a plurality of pulse generators, and the transmission circuit 3 adjusts the amount of delay of each drive signal so that ultrasonic waves transmitted from the plurality of transducers of the transducer array 2 form an ultrasound beam on the basis of a transmission delay pattern selected according to the control signal from the device control unit 15, and supplies the obtained signals to the plurality of transducers. Thus, in a case where a pulsed or continuous-wave voltage is applied to the electrodes of the transducers of the transducer array 2, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 2 of the ultrasound probe 21. The ultrasonic waves propagating toward the transducer array 2 in this manner are received by each transducer constituting the transducer array 2. In this case, each transducer constituting the transducer array 2 expands and contracts by receiving the propagating ultrasound echo to generate electrical signals, and outputs the electrical signals to the reception circuit 4.

Figure 2:
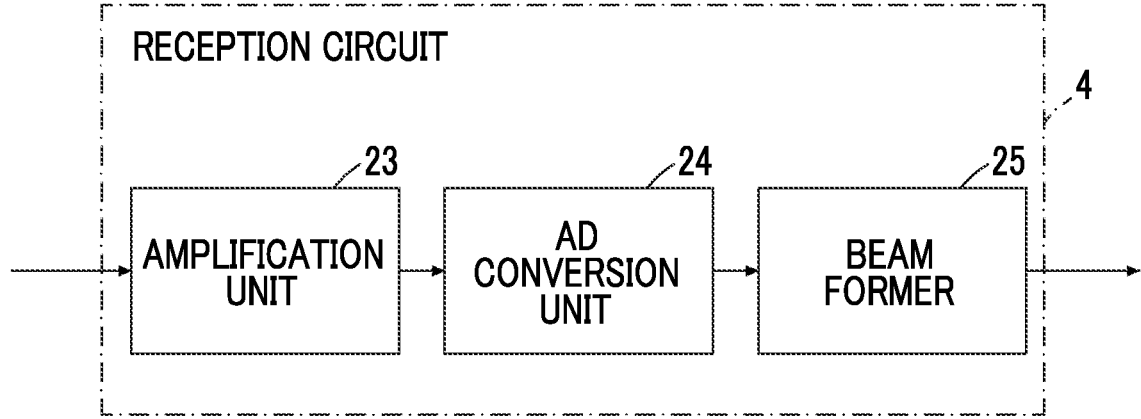
FIG. 2 is a block diagram illustrating an internal configuration of a reception circuit in the first embodiment of the present invention.

The reception circuit 4 performs processing on the signals output from the transducer array 2 according to the control signal from the device control unit 15 to generate reception data, which is so-called radio frequency (RF) data. As illustrated in FIG. 2, the reception circuit 4 has a configuration in which an amplification unit 23, an analog digital (AD) conversion unit 24, and a beam former 25 are connected in series.

The amplification unit 23 amplifies the signals input from each transducer constituting the transducer array 2, and transmits the amplified signals to the AD conversion unit 24. The AD conversion unit 24 converts the signals transmitted from the amplification unit 23 into digital data, and transmits the data to the beam former 25. The beam former 25 performs so-called reception focusing processing in which addition is performed by giving delays to respective pieces of data converted by the AD conversion unit 24 according to a sound speed distribution or a sound speed set on the basis of a reception delay pattern selected according to the control signals from the device control unit 15. Through the reception focusing processing, reception data in which each piece of data converted by the AD conversion unit 24 is phased and added and the focus of the ultrasound echo is narrowed is acquired.

Figure 3:
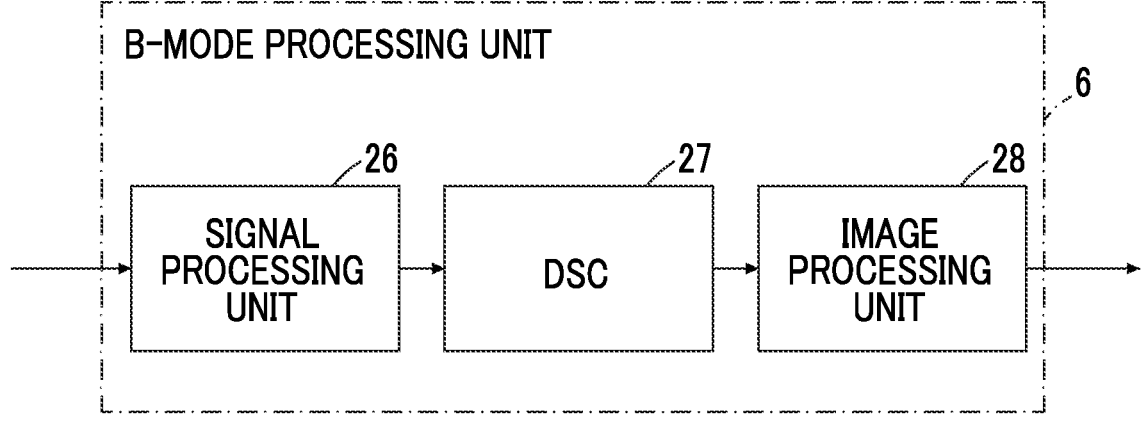
FIG. 3 is a block diagram illustrating an internal configuration of a B-mode processing unit in the first embodiment of the present invention.

As illustrated in FIG. 3, the B-mode processing unit 6 has a configuration in which a signal processing unit 26, a digital scan converter (DSC) 27, and an image processing unit 28 are sequentially connected in series.

The signal processing unit 26 generates a B-mode image signal, which is tomographic image information regarding tissues inside the subject, by performing, on reception data generated by the reception circuit 4, correction of the attenuation due to the distance according to the depth of the reflection position of the ultrasonic wave and then performing envelope detection processing.

The DSC 27 converts (raster conversion) the B-mode image signal generated by the signal processing unit 26 into an image signal according to a normal television signal scanning method.

The image processing unit 28 performs various kinds of necessary image processing such as gradation processing on the B-mode image signal input from the DSC 27, and then outputs the B-mode image signal to the display control unit 8. In the following, the B-mode image signal subjected to the image processing by the image processing unit 28 is simply referred to as a B-mode image.

Figure 4:
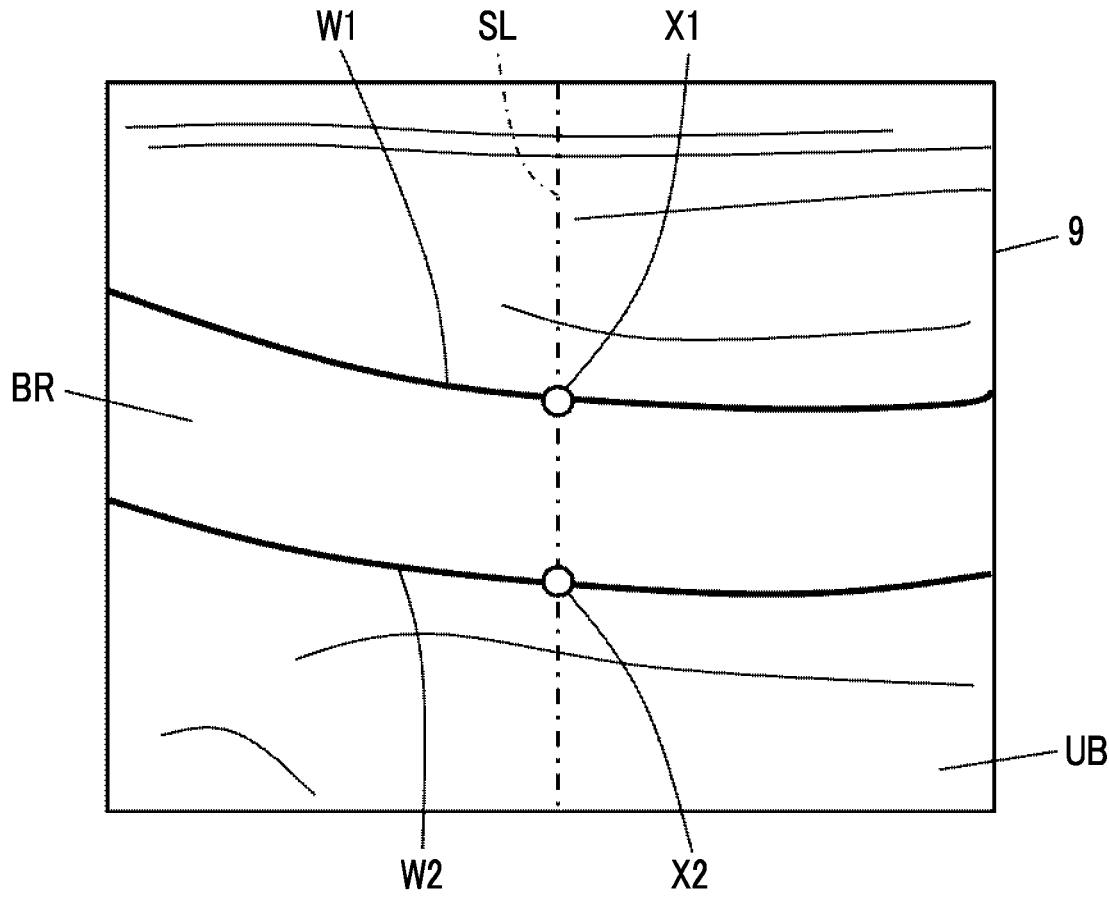
FIG. 4 is a diagram schematically illustrating a method of detecting a vascular wall on a B-mode image in the first embodiment of the present invention.

The vascular wall detection unit 10 detects a vascular wall of the blood vessel included in the B-mode image by analyzing the B-mode image generated by the B-mode processing unit 6. As illustrated in FIG. 4, the vascular wall detection unit 10 performs an image analysis on the entire B-mode image UB, recognizes a long-axis image of the blood vessel, and recognizes the position of the vascular wall in the recognized blood vessel. Further, the vascular wall detection unit 10 detects a position where a brightness change in the vertical direction is the largest in the B-mode image UB, and sets a virtual search line SL that passes through the detected position and is along the vertical direction of the B-mode image UB. Here, the long-axis image of the blood vessel refers to a longitudinal cross section of the blood vessel along a traveling direction of the blood vessel.

The vascular wall detection unit 10 can detect positions of two points X1 and X2, where the brightness change of the B-mode image UB is greater than a certain value, on the search line SL as a position of an anterior vascular wall W1 and a position of a posterior vascular wall W2 on the basis of a brightness profile of the B-mode image UB on the search line SL.

In a case of recognizing the long-axis image of the blood vessel, the vascular wall detection unit 10 can recognize the long-axis image of the blood vessel on the B-mode image UB by using a known algorithm. For example, the vascular wall detection unit 10 can store typical pattern data of the blood vessel region in advance as a template, calculate a similarity degree for the pattern data while searching the image using the template, and consider that the blood vessel region is present in a place where the similarity degree is equal to or greater than a threshold value and is the maximum.

Further, for the calculation of the similarity degree, in addition to simple template matching, for example, a machine learning method described in Csurka et al.: Visual Categorization with Bags of Keypoints, Proc. of ECCV Workshop on Statistical Learning in Computer Vision, pp. 59-74 (2004) or a general image recognition method using deep learning described in Krizhevsk et al.: ImageNet Classification with Deep Convolutional Neural Networks, Advances in Neural Information Processing Systems 25, pp. 1106-1114 (2012) can be used.

Figure 5:
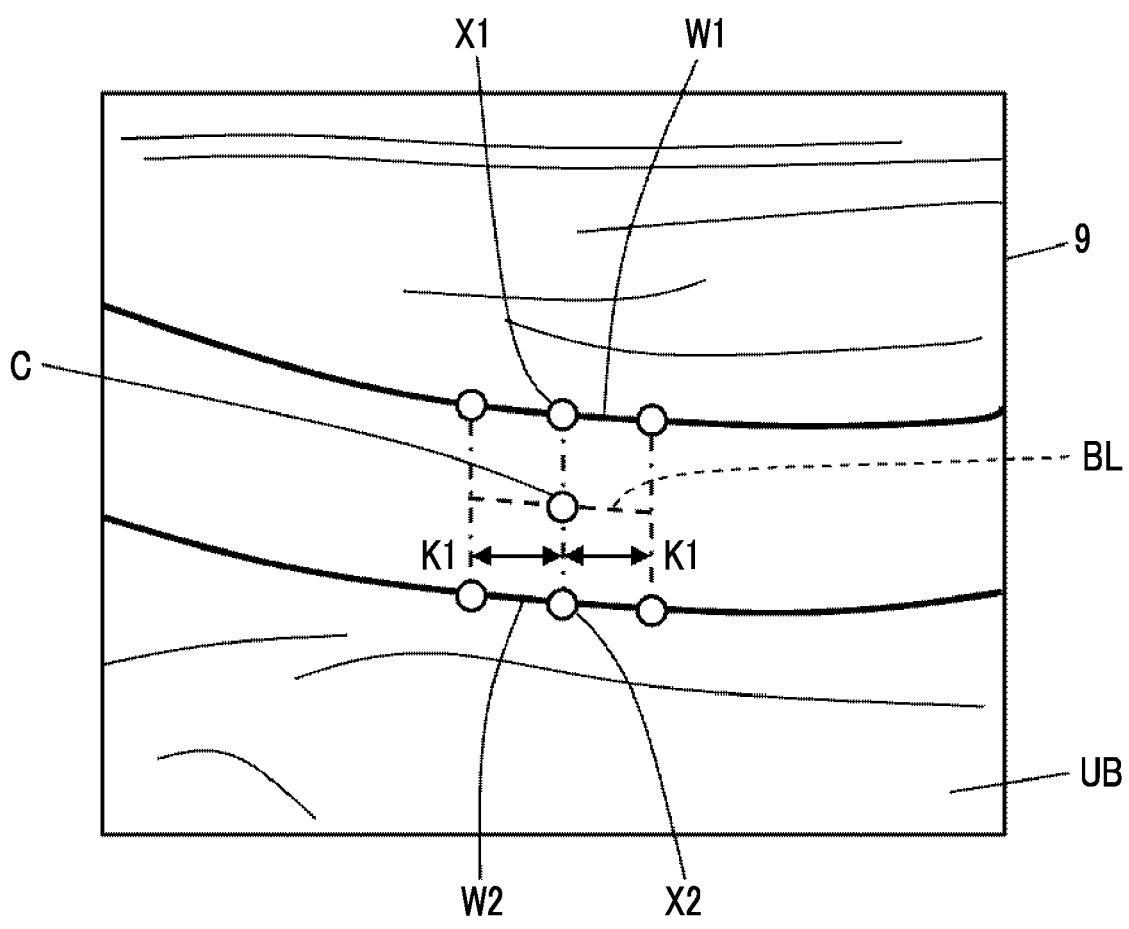
FIG. 5 is a diagram schematically illustrating a method of estimating a gradient of a blood vessel on the B-mode image in the first embodiment of the present invention.

The vascular wall detection unit 10 estimates a blood vessel traveling angle in the B-mode image UB. For example, as illustrated in FIG. 5, the vascular wall detection unit 10 searches for the anterior vascular wall W1 in a shallow direction and searches for the posterior vascular wall W2 in a deep direction, at a plurality of positions in a range having a constant distance K1 in a lateral direction of the B-mode image UB, that is, in an orientation direction from a midpoint C of the positions of the two points X1 and X2 detected as the position of the anterior vascular wall W1 and the position of the posterior vascular wall W2, estimates a straight line passing through the plurality of positions of the detected anterior vascular wall W1 and a straight line passing through the plurality of positions of the posterior vascular wall W2, and thereby can estimate an inclination of the blood vessel. In the example illustrated in FIG. 5, a virtual blood vessel gradient line BL representing the gradient of the blood vessel is obtained by averaging the inclination of straight line estimated for the anterior vascular wall W1 and the inclination of the straight line estimated for the posterior vascular wall W2.

Figure 6:
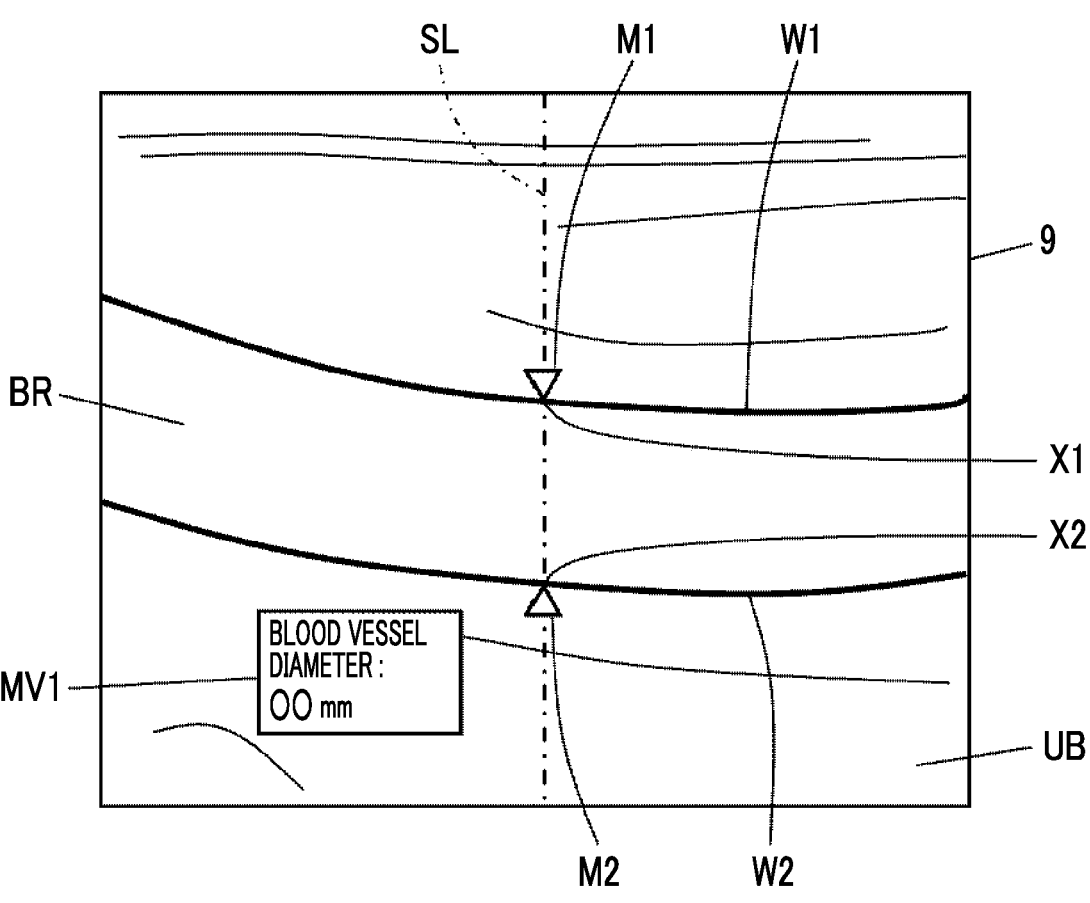
FIG. 6 is a diagram schematically illustrating a state in which a detection point marker disposed on a straight line in a vertical direction on the B-mode image and a measurement value of a blood vessel diameter are displayed on a display device in the first embodiment of the present invention.

As illustrated in FIG. 6, the vascular wall detection unit 10 can dispose detection point markers M1 and M2 representing the points detected as the vascular wall, at the position of the point X1, which is detected as the position of the anterior vascular wall W1, and the position of the point X2, which is detected as the position of the posterior vascular wall W2, on the search line SL in the B-mode image UB, and cause the display device 9 to display the disposed detection point markers M1 and M2.

Further, the vascular wall detection unit 10 can measure the distance between the two disposed detection point markers M1 and M2 as the blood vessel diameter, and cause the display device 9 to display a measurement value MV1 of the blood vessel diameter which is measured.

Figure 7:
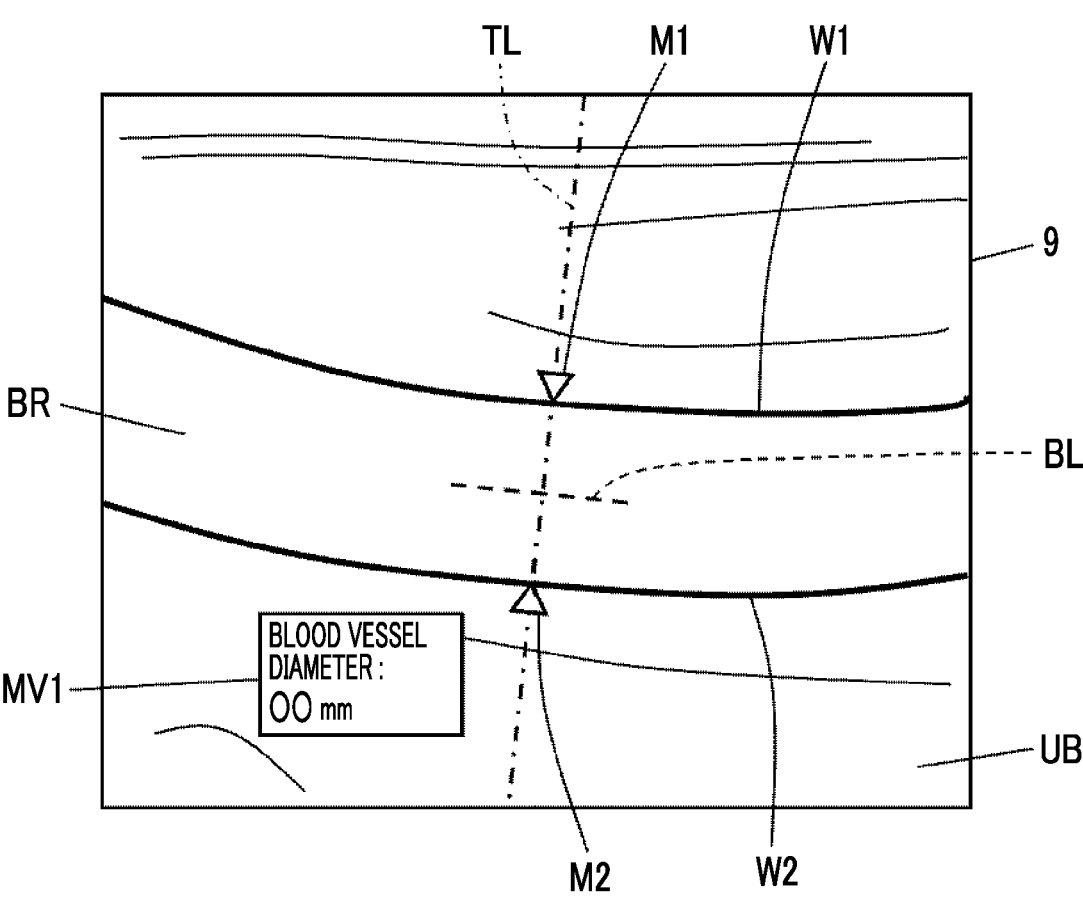
FIG. 7 is a diagram schematically illustrating a state in which the detection point marker disposed on a straight line orthogonal to the gradient of the blood vessel on the B-mode image and the measurement value of the blood vessel diameter are displayed on the display device in the first embodiment of the present invention.

As illustrated in FIG. 7, the vascular wall detection unit 10 can dispose the detection point marker M1 at the position of an intersection between a straight line TL orthogonal to the blood vessel gradient line BL and the anterior vascular wall W1, dispose the detection point marker M2 at the position of an intersection between the straight line TL and the posterior vascular wall W2, and cause the display device 9 to display the two disposed detection point markers M1 and M2. In this case, the vascular wall detection unit 10 measures the distance between the two detection point markers M1 and M2 disposed on the straight line TL as the blood vessel diameter, and therefore, it is possible to more accurately measure the blood vessel diameter.

The vascular wall detection unit 10 calculates a cross-sectional area of the blood vessel on the basis of the measured blood vessel diameter, assuming that the blood vessel has a circular cross section.

Figure 8:
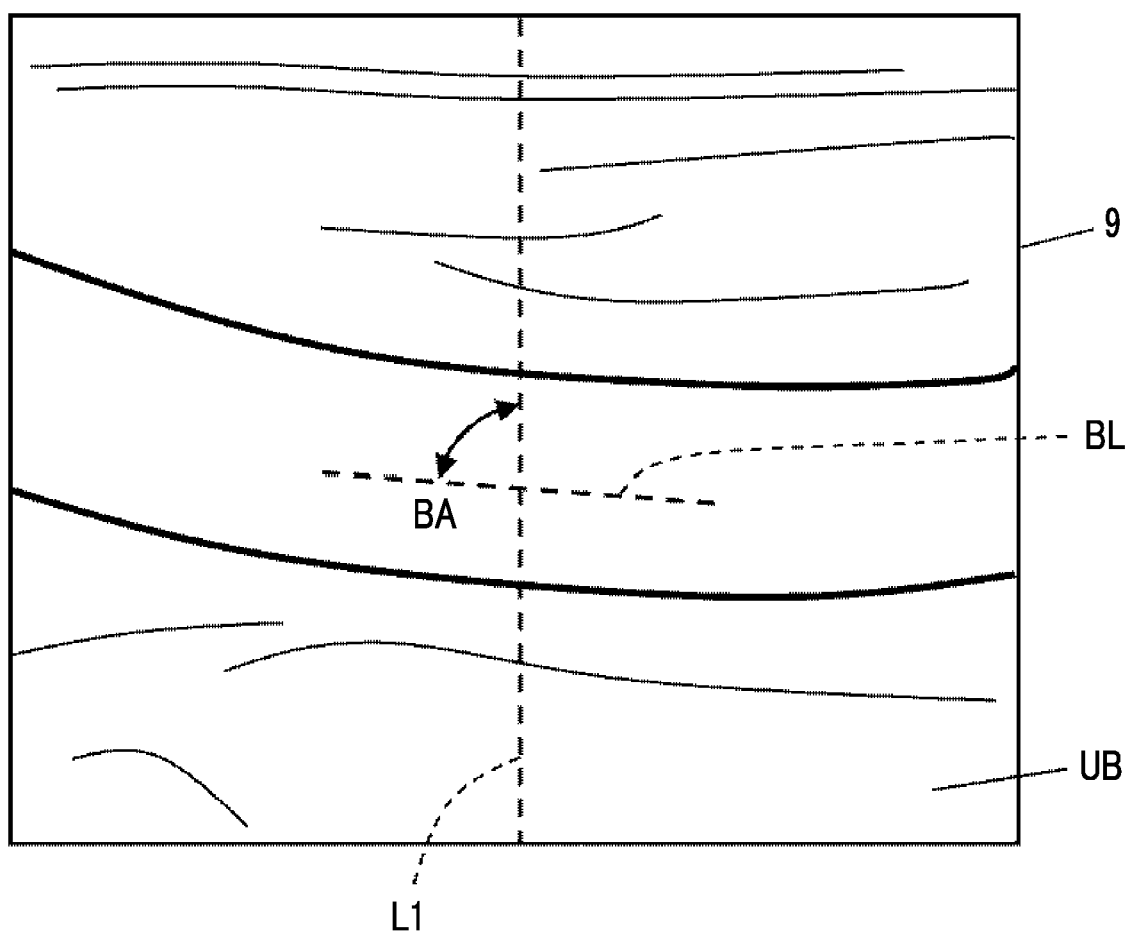
FIG. 8 is a diagram schematically illustrating an estimated traveling angle of the blood vessel on the B-mode image in the first embodiment of the present invention.

For example, as illustrated in FIG. 8, the vascular wall detection unit 10 can estimate an angle between the obtained blood vessel gradient line BL and a straight line L1 along the vertical direction of the B-mode image UB, as a blood vessel traveling angle BA.

Figures 9, 10:
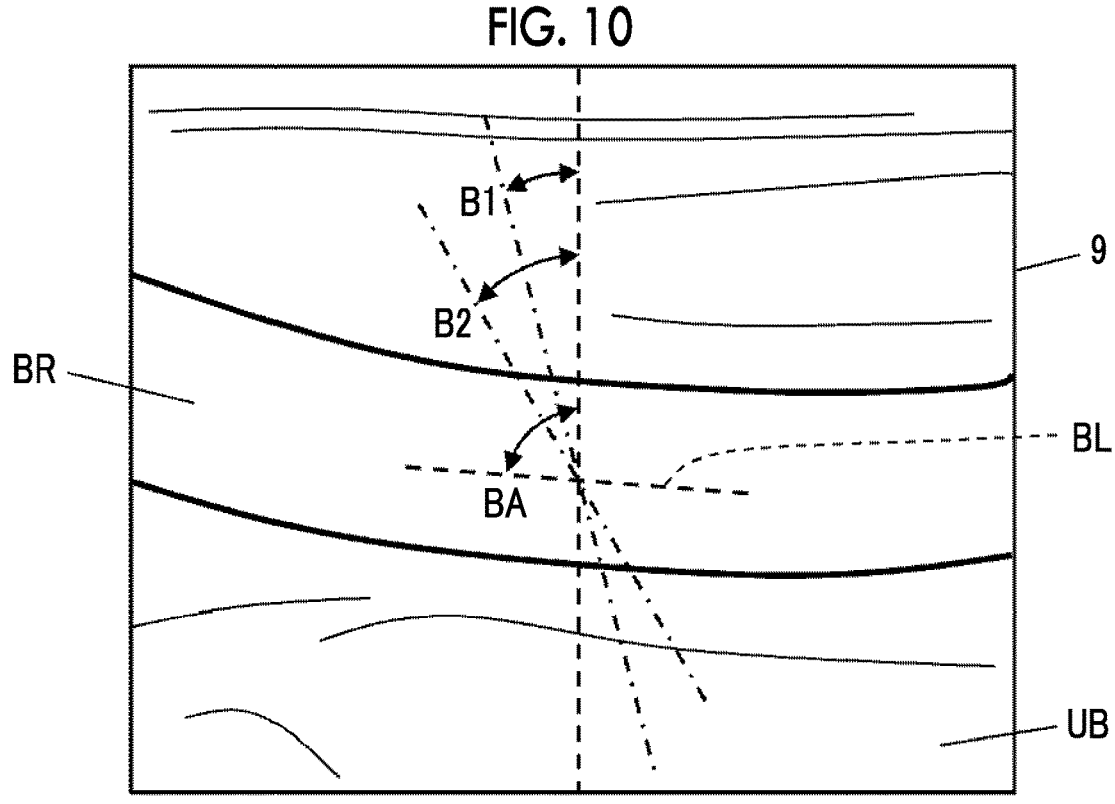
FIG. 9 is a diagram schematically illustrating a method of setting a B-mode steer angle in the first embodiment of the present invention.
FIG. 10 is a diagram schematically illustrating a method of setting a Doppler steer angle in the first embodiment of the present invention.

The vascular wall detection unit 10 sets a B-mode steer angle by using the estimated blood vessel traveling angle BA. For example, as illustrated in FIG. 9, an angle A1 or the like is set as the B-mode steer angle. The B-mode steer angle is defined as an angle between a scan line when the B-mode image UB is generated by the B-mode processing unit 6 and the straight line L1 in the vertical direction in the B-mode image UB. Here, in order to obtain the B-mode image UB in which the anterior vascular wall W1 and the posterior vascular wall W2 are clearly shown, the vascular wall detection unit 10 sets the B-mode steer angle such that an angle between the scan line when generating the B-mode image UB and the blood vessel gradient line BL approaches 90 degrees.

For example, using the blood vessel traveling angle BA, the fixed angle A1, and a fixed angle A2 greater than the angle A1, the vascular wall detection unit 10 can set the B-mode steer angle to 0 degrees in a case where a relationship of 90−BA<A1/2 is satisfied, set the B-mode steer angle to the angle A1 as illustrated in FIG. 9 in a case where a relationship of A1/2≤90−BA<A2/2 is satisfied, and set the B-mode steer angle to the angle A2 in a case where a relationship of A2/2≤90−BA is satisfied. Here, for example, the angle A1 can be set to 7.5 degrees in advance, and the angle A2 can be set to 15 degrees in advance.

The vascular wall detection unit 10 sets a Doppler steer angle by using the estimated blood vessel traveling angle BA. For example, as illustrated in FIG. 10, an angle B1, an angle B2, or the like is set as the Doppler steer angle. Here, the Doppler steer angle refers to an inclination angle of the scan line when the Doppler data is acquired.

Figure 11:
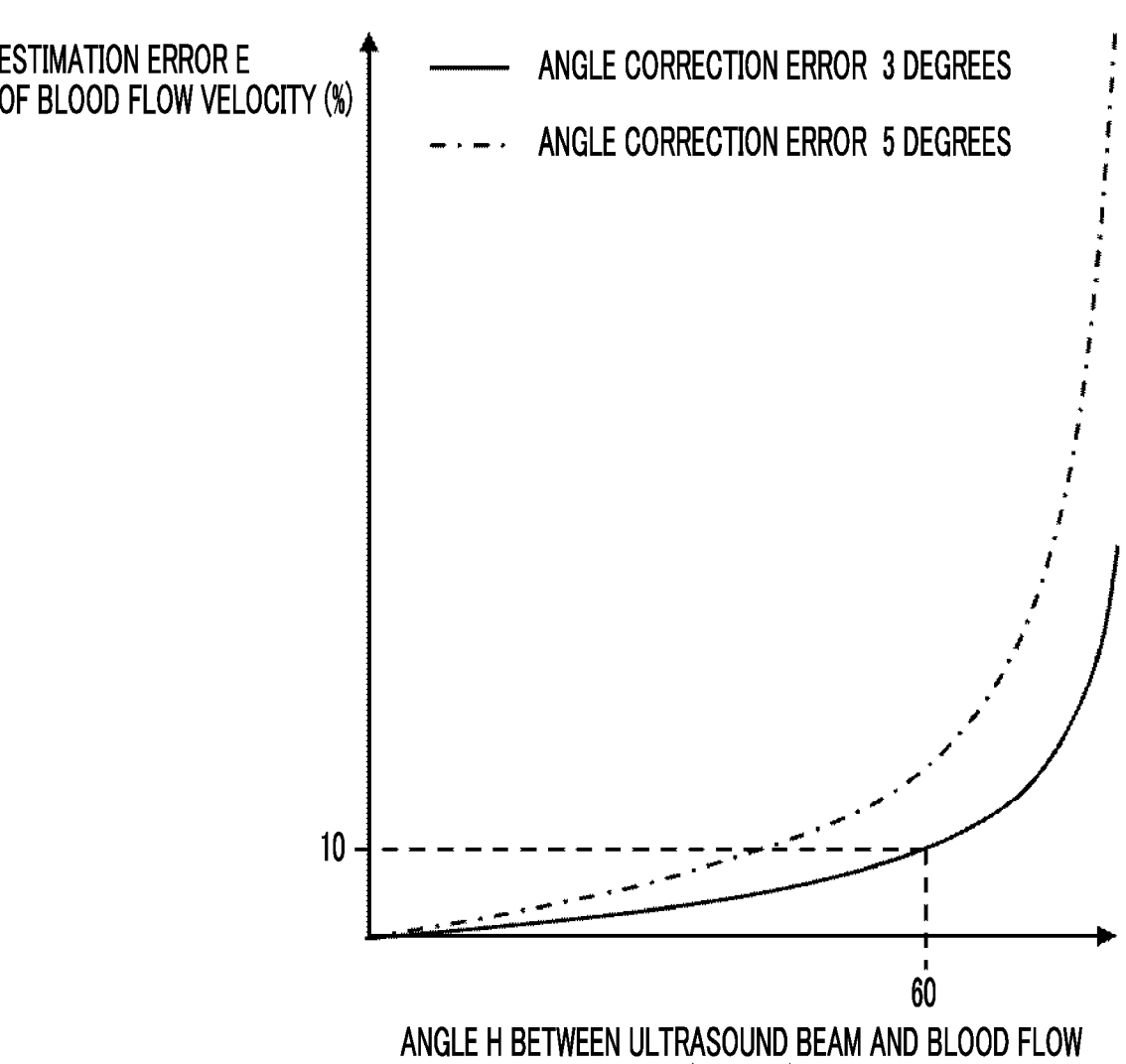
FIG. 11 is a graph illustrating a relationship between an angle between an ultrasound beam and a blood flow and an estimation error of a blood flow velocity in the first embodiment of the present invention.

Here, it is known that there is a relationship as illustrated in FIG. 11 between an angle H, which is between the blood flow in the blood vessel and the ultrasound beam transmitted toward the blood vessel in order to acquire the Doppler data, and an estimation error E of the blood flow velocity to be calculated on the basis of the acquired Doppler data. According to the relationship, it can be seen that as the angle H of the ultrasound beam with respect to the blood flow is larger, the estimation error E of the blood flow velocity is increased exponentially. Further, it can be seen that as an error of angle correction for the blood vessel traveling angle is larger, the estimation error E of the blood flow velocity is increased.

Regarding the angle H between the ultrasound beam and the blood flow and the estimation error E of the blood flow velocity, it is known that, for example, in a case where the angle H between the ultrasound beam and the blood flow is held within 60 degrees, the estimation error E of the blood flow velocity is within 10% and the blood flow velocity can be accurately obtained even in a case where there is an error of 3 degrees in the angle correction for the blood vessel traveling angle. Thus, the vascular wall detection unit 10 sets the Doppler steer angle such that an angle correction value for the blood vessel traveling angle BA, that is, an angle between the scan line and the blood vessel gradient line BL is within 60 degrees, in order to accurately calculate the blood flow velocity.

For example, using the blood vessel traveling angle BA, and the fixed angle B1 and the angle B2 greater than the angle B1 as illustrated in FIG. 10, the vascular wall detection unit 10 can set the Doppler steer angle to 0 degrees in a case where a relationship of BA<60 is satisfied, set the Doppler steer angle to the angle B1 in a case where a relationship of 60≤B<60+B1 is satisfied, and set the Doppler steer angle to the angle B2 in a case where a relationship of 60+B1≤BA is satisfied. Here, for example, the angle B1 can be set to 15 degrees in advance, and the angle B2 can be set to 30 degrees in advance.

Figures 12, 13:
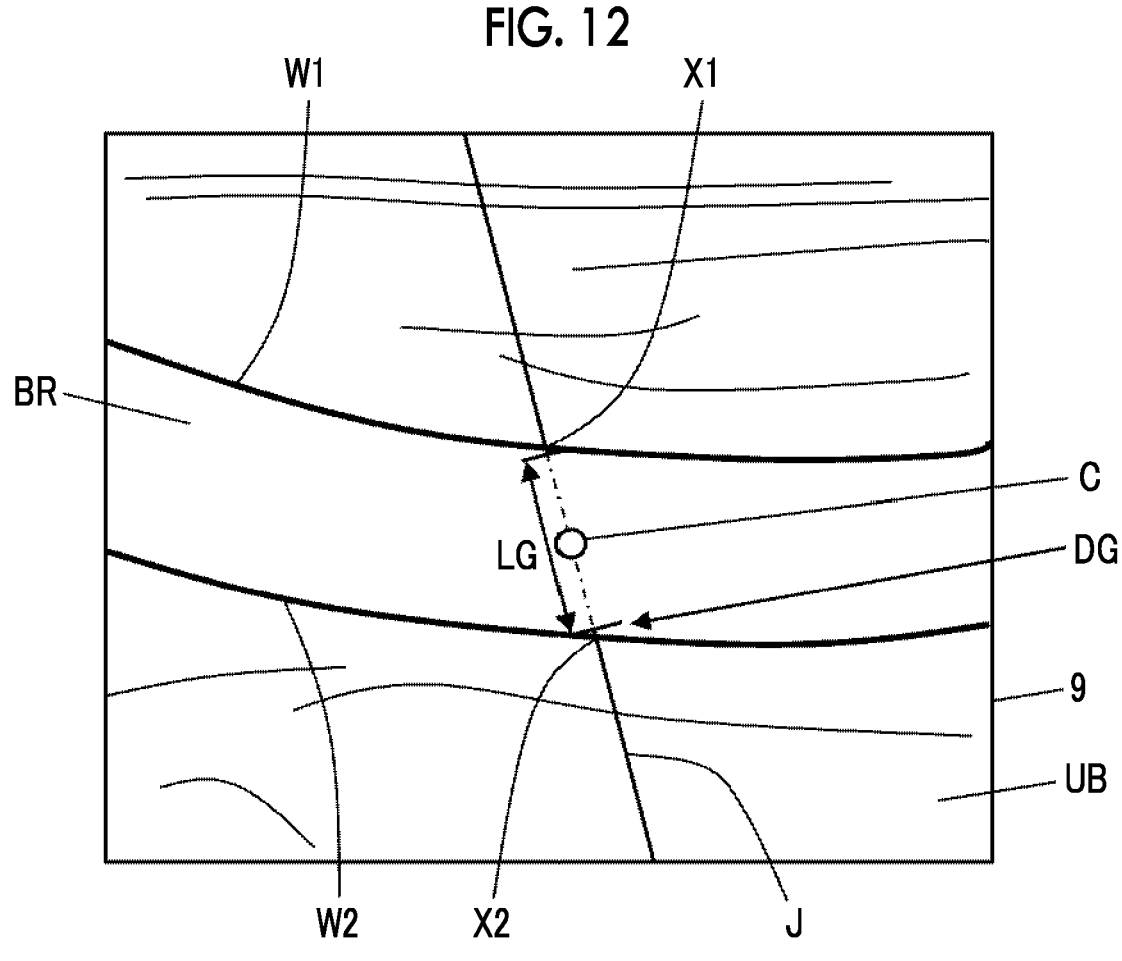
FIG. 12 is a diagram schematically illustrating the B-mode image and the Doppler gate set on the B-mode image displayed on the display device in the first embodiment of the present invention.
FIG. 13 is a block diagram illustrating an internal configuration of a Doppler processing unit in the first embodiment of the present invention.

As illustrated in FIG. 12, the gate setting unit 11 sets the Doppler gate DG having a size and a center position decided on the basis of the coordinates of the anterior vascular wall W1 and the coordinates of the posterior vascular wall W2 detected by the vascular wall detection unit 10, in the blood vessel region BR on the B-mode image UB. In this case, the gate setting unit 11 can set, as the center position of the Doppler gate DG, the midpoint C of the positions of the two points X1 and X2 detected as the position of the anterior vascular wall W1 and the position of the posterior vascular wall W2 by the vascular wall detection unit 10, and set the Doppler gate DG on a straight line J that passes through the midpoint C and is inclined by the set Doppler steer angle. The straight line J corresponds to the scan line. The gate setting unit 11 can set the length calculated by multiplying the blood vessel diameter measured by the vascular wall detection unit 10 by a fixed value, as a gate width LG of the Doppler gate DG. Here, the fixed value to be multiplied by the blood vessel diameter is a number greater than zero such as 0.75 and equal to or less than 1.00, and is decided by the user's input operation through the input device 16, for example.

Further, as illustrated in FIG. 12, the gate setting unit 11 causes the display device 9 to display the set Doppler gate DG on the B-mode image UB in a superimposed manner.

The Doppler processing unit 7 acquires the Doppler data in the Doppler gate DG set in the blood vessel region BR by the gate setting unit 11, and generates the Doppler waveform image on the basis of the acquired Doppler data. As illustrated in FIG. 13, the Doppler processing unit 7 has a configuration in which a quadrature detection unit 29, a high-pass filter 30, a fast Fourier transformer 31, and a Doppler waveform image generation unit 32 are sequentially connected in series and a data memory 33 is connected to an output terminal of the quadrature detection unit 29.

The quadrature detection unit 29 mixes the reception data generated by the reception circuit 4 with a carrier signal having a reference frequency to perform quadrature detection on the reception data and converts the reception data into complex data.

The high-pass filter 30 functions as a so-called wall filter, and removes a frequency component derived from the motion of the body tissue inside the subject, from the complex data generated by the quadrature detection unit 29.

The fast Fourier transformer 31 performs a Fourier transform on the complex data of a plurality of sample points to perform frequency analysis, obtains the blood flow velocity, and generates a spectrum signal.

The Doppler waveform image generation unit 32 generates a Doppler waveform image signal by aligning the spectrum signals generated by the fast Fourier transformer 31 on a time axis and expressing the magnitude of each frequency component in brightness. In the following, the Doppler waveform image signal generated by the Doppler waveform image generation unit 32 is simply referred to as a Doppler waveform image.

Further, the data memory 33 saves the complex data converted from the reception data by the quadrature detection unit 29.

The blood flow velocity calculation unit 13 calculates the blood flow velocity by a so-called pulse Doppler method on the basis of the Doppler data acquired by the Doppler processing unit 7. The blood flow velocity calculation unit 13 can calculate an average blood flow velocity in each heartbeat period.

The blood flow rate measurement unit 12 measures a blood flow rate representing the volume of the blood flowing in the blood vessel per unit time on the basis of the cross-sectional area of the blood vessel calculated by the vascular wall detection unit 10 and the blood flow velocity calculated by the blood flow velocity calculation unit 13.

The device control unit 15 controls each unit of the ultrasound diagnostic apparatus 1 on the basis of a program stored in advance in the storage unit 17 or the like and the user's input operation through the input device 16.

The display control unit 8 performs predetermined processing on the B-mode image UB generated by the B-mode processing unit 6 and the Doppler waveform image generated by the Doppler processing unit 7, and causes the display device 9 to display the B-mode image UB and the Doppler waveform image, under the control of the device control unit 15.

The display device 9 is for displaying the B-mode image UB, the Doppler waveform image, and the like under the control of the display control unit 8, and includes a display device such as a liquid crystal display (LCD), or an organic electroluminescence (EL) display.

The input device 16 is for the user to perform an input operation, and can be configured to comprise a keyboard, a mouse, a trackball, a touchpad, a touch panel, and the like.

The storage unit 17 stores an operation program and the like of the ultrasound diagnostic apparatus 1, and recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The processor 22 having the B-mode processing unit 6, the Doppler processing unit 7, the display control unit 8, the vascular wall detection unit 10, the gate setting unit 11, the blood flow rate measurement unit 12, the blood flow velocity calculation unit 13, and the device control unit 15 is configured by a central processing unit (CPU) and a control program for causing the CPU to execute various kinds of processing, but the processor 22 may be configured by using a field programmable gate array (FPGA), a digital signal processor (DSP), an application specific integrated circuit (ASIC), a graphics processing unit (GPU), or other integrated circuits (IC) or may be configured by a combination thereof.

In addition, the B-mode processing unit 6, the Doppler processing unit 7, the display control unit 8, the vascular wall detection unit 10, the gate setting unit 11, the blood flow rate measurement unit 12, the blood flow velocity calculation unit 13, and the device control unit 15 of the processor 22 can also be configured by being integrated partially or entirely into one CPU or the like.

The ultrasound diagnostic apparatus 1 according to the first embodiment of the present invention automatically measures the blood flow rate in the subject on the basis of a determined start trigger. In the following, the operation of the ultrasound diagnostic apparatus 1 in the first embodiment will be described in detail using the flowchart illustrated in FIG. 14.

First, in Step S1, the B-mode image UB in which at least the blood vessel is imaged is generated, the generated B-mode image UB is displayed on the display device 9. In this case, an ultrasound beam is transmitted from the plurality of transducers of the transducer array 2 according to the drive signal from the transmission circuit 3, the reception signal is output to the reception circuit 4 from each transducer which has received the ultrasound echo from the subject, is amplified in the amplification unit 23, is subjected to the AD conversion in the AD conversion unit 24, and is phased and added in the beam former 25, and thereby the reception data is generated. The reception data is subjected to the envelope detection processing by the signal processing unit 26 to become the B-mode image signal in the B-mode processing unit 6, and is output to the display control unit 8 via the DSC 27 and the image processing unit 28, and the B-mode image UB is displayed on the display device 9 under the control of the display control unit 8. Also in the subsequent steps, in this manner, the B-mode images UB are continuously generated, and the generated B-mode images UB are displayed on the display device 9.

In Step S2, the vascular wall detection unit 10 performs the image analysis on the B-mode images UB of a plurality of frames continuously generated in Step S1, and recognizes the long-axis image of the blood vessel in the B-mode image UB. In Step S2, it is determined whether the position of the long-axis image of the blood vessel recognized by the vascular wall detection unit 10 is stable for each of the B-mode images UB continuously generated in Step S1. In this case, in the B-mode images UB of the plurality of frames generated for a fixed time such as one second, for example, in a case where the change in position of the long-axis image of the blood vessel is equal to or less than a fixed value such as 0.2 mm, it is determined that the position of the long-axis image of the blood vessel is stable. Further, in the B-mode images UB of the plurality of frames generated for a fixed time such as one second, for example, in a case where the change in position of the long-axis image of the blood vessel is greater than a fixed value such as 0.2 mm, it is determined that the position of the long-axis image of the blood vessel is not stable.

In a case where it is determined in Step S2 that the position of the long-axis image of the blood vessel is not stable, the processing of Step S2 is performed again so that the long-axis image of the blood vessel in newly generated B-mode images UB of a plurality of frames is recognized, and it is determined whether the position of the long-axis image of the blood vessel is stable. In a case where it is determined in Step S2 that the position of the long-axis image of the blood vessel is stable, the processing proceeds to Step S3.

In this manner, with a time point at which the amount of change of the long-axis image of the blood vessel in the B-mode image UB is equal to or less than a fixed value as the start trigger, the operation of automatically measuring the blood flow rate is performed in Step S3 and subsequent steps.

In Step S3, the vascular wall detection unit 10 detects the vascular wall of the blood vessel included in the B-mode image UB by analyzing the B-mode image UB generated in Step S1. For example, as illustrated in FIG. 4, the vascular wall detection unit 10 detects a position where the brightness change in the vertical direction is the largest in the B-mode image UB, detects the vascular wall of the blood vessel recognized in Step S2, and sets the search line SL that passes through the detected position and is along the vertical direction of the B-mode image UB. The vascular wall detection unit 10 can detect the positions of the two points X1 and X2, where the brightness change of the B-mode image UB is greater than a certain value, on the search line SL as the position of the anterior vascular wall W1 and the position of the posterior vascular wall W2 on the basis of the brightness profile of the B-mode image UB on the search line SL.

In Step S4, the vascular wall detection unit 10 estimates the gradient of the blood vessel in the B-mode image, and estimates the blood vessel traveling angle BA from the estimated gradient of the blood vessel. For example, as illustrated in FIG. 5, the vascular wall detection unit 10 searches for the anterior vascular wall W1 in the shallow direction and searches for the posterior vascular wall W2 in the deep direction, at the positions in a range having a constant distance K1 in the orientation direction of the B-mode image UB from the midpoint C of the positions of the two detected points X1 and X2 on the B-mode image UB, estimates a straight line passing through the plurality of positions of the detected anterior vascular wall W1 and a straight line passing through the plurality of positions of the posterior vascular wall W2, averages the inclination of the straight line estimated for the anterior vascular wall W1 and the inclination of the straight line estimated for the posterior vascular wall W2, and thereby can estimate a virtual blood vessel gradient line BL representing the gradient of the blood vessel.

Further, as illustrated in FIG. 8, the vascular wall detection unit 10 can estimate an angle between the obtained blood vessel gradient line BL and the straight line L1 along the vertical direction of the B-mode image UB, as the blood vessel traveling angle BA.

In Step S5, as illustrated in FIG. 6, the vascular wall detection unit 10 can dispose the detection point markers M1 and M2 representing the points detected as the vascular wall, at the positions of the two points X1 and X2 detected as the position of the anterior vascular wall W1 and the position of the posterior vascular wall W2 in Step S3, and cause the display device 9 to display the disposed detection point markers M1 and M2.

As illustrated in FIG. 7, the vascular wall detection unit 10 can dispose the detection point marker M1 at the position of an intersection between a straight line TL orthogonal to the blood vessel gradient line BL estimated in Step S4 and the anterior vascular wall W1, dispose the detection point marker M2 at the position of an intersection between the straight line TL and the posterior vascular wall W2, and cause the display device 9 to display the two disposed detection point markers M1 and M2.

In subsequent Step S6, it is determined whether the positions of the detection point markers M1 and M2 disposed on the B-mode image UB in Step S5 are stable for each B-mode image UB generated by the B-mode processing unit 6. In this case, in the B-mode images UB of the plurality of frames generated for a fixed time such as one second after the detection point markers M1 and M2 are displayed on the display device 9, for example, in a case where the change in positions of the detection point markers M1 and M2 is equal to or less than a fixed value such as 0.2 mm, it is determined that the positions of the detection point markers M1 and M2 are stable. Further, in the B-mode images UB of the plurality of frames generated for a fixed time such as one second after the detection point markers M1 and M2 are displayed on the display device 9, for example, in a case where the change in positions of the detection point markers M1 and M2 is greater than a fixed value such as 0.2 mm, it is determined that the positions of the detection point markers M1 and M2 are not stable.

In a case where it is determined in Step S6 that the positions of the detection point markers M1 and M2 are not stable, the processing of Step S6 is performed again so that it is determined whether the positions of the detection point markers M1 and M2 in newly generated B-mode images UB of a plurality of frames are stable. In a case where it is determined in Step S6 that the positions of the detection point markers M1 and M2 are stable, the processing proceeds to Step S7.

In Step S7, the vascular wall detection unit 10 measures the distance between the two disposed detection point markers M1 and M2 as the blood vessel diameter, and causes the display device 9 to display the measurement value MV1 of the blood vessel diameter which is measured, as illustrated in FIG. 6 or FIG. 7, for example. Here, for example, in Step S5, in a case where the detection point markers M1 and M2 are disposed on the straight line TL orthogonal to the blood vessel gradient line BL, it is possible to obtain a more accurate blood vessel diameter.

Also in the subsequent steps, the processing of Step S3 to Step S7 is executed each time the B-mode image UB is generated by the B-mode processing unit 6.

In subsequent Step S8, the vascular wall detection unit 10 sets the B-mode steer angle representing the inclination angle of the scan line when the B-mode image UB is generated by the B-mode processing unit 6, by using the blood vessel traveling angle BA estimated in Step S4. In this case, for example, using the blood vessel traveling angle BA, and the fixed angle A1 and the fixed angle A2 greater than the angle A1 illustrated in FIG. 9, the vascular wall detection unit 10 can set the B-mode steer angle to 0 degrees in a case where a relationship of 90−BA<A1/2 is satisfied, set the B-mode steer angle to the angle A1 in a case where a relationship of A1/2≤90−BA<A2/2 is satisfied, and set the B-mode steer angle to the angle A2 in a case where a relationship of A2/2≤90−BA is satisfied. Here, for example, the angle A1 can be set to 7.5 degrees in advance, and the angle A2 can be set to 15 degrees in advance.

In Step S9, the vascular wall detection unit 10 sets the Doppler steer angle representing the inclination angle of the scan line when the Doppler data is acquired by the Doppler processing unit 7, by using the blood vessel traveling angle BA estimated in Step S4. In this case, for example, using the blood vessel traveling angle BA, and the fixed angle B1 and the angle B2 greater than the angle B1 as illustrated in FIG. 10, the vascular wall detection unit 10 can set the Doppler steer angle to 0 degrees in a case where a relationship of BA<60 is satisfied, set the Doppler steer angle to the angle B1 in a case where a relationship of 60≤BA<60+B1 is satisfied, and set the Doppler steer angle to the angle B2 in a case where a relationship of 60+B1≤BA is satisfied. Here, for example, the angle B1 can be set to 15 degrees in advance, and the angle B2 can be set to 30 degrees in advance.

In Step S10, as illustrated in FIG. 12, the gate setting unit 11 sets the Doppler gate DG having a size and a center position decided on the basis of the coordinates of the anterior vascular wall W1 and the coordinates of the posterior vascular wall W2 detected in Step S3, in the blood vessel region BR on the B-mode image UB. In this case, the gate setting unit 11 can set, as the center position of the Doppler gate DG, the midpoint C of the positions of the two points X1 and X2 detected as the position of the anterior vascular wall W1 and the position of the posterior vascular wall W2 in Step S3, and set the length calculated by multiplying the blood vessel diameter measured in Step S7 by a fixed value, as the gate width LG of the Doppler gate DG. Here, the fixed value to be multiplied by the blood vessel diameter is a number greater than zero such as 0.75 and equal to or less than 1.00, and is decided by the user's input operation through the input device 16, for example.

Further, as illustrated in FIG. 12, the gate setting unit 11 causes the display device 9 to display the set Doppler gate DG on the B-mode image UB in a superimposed manner.

Similar to the processing of Step S6, in Step S11, it is determined whether the positions of the detection point markers M1 and M2 disposed on the B-mode image UB in Step S5 are stable for each B-mode image UB generated by the B-mode processing unit 6. In a case where it is determined in Step S11 that the positions of the detection point markers M1 and M2 are not stable, the processing of Step S11 is performed again so that it is determined whether the positions of the detection point markers M1 and M2 in newly generated B-mode images UB of a plurality of frames are stable. In a case where it is determined in Step S11 that the positions of the detection point markers M1 and M2 are stable, the processing proceeds to Step S12.

In Step S12, the Doppler processing unit 7 starts to continuously generate the Doppler waveform images UD, and causes the display device 9 to display the generated Doppler waveform images UD. In this case, the Doppler processing unit 7 acquires the Doppler data in the Doppler gate DG set in Step S10 as illustrated in FIG. 12, continuously generates the Doppler waveform images UD on the basis of the acquired Doppler data, and causes the display device 9 to display the generated Doppler waveform images UD. Thereby, both the B-mode image UB and the Doppler waveform image UD are continuously generated, and as illustrated in FIG. 15, the B-mode image UB and the Doppler waveform image UD are displayed on the display device 9.

In Step S13, the adjustment of the Doppler waveform WD in the Doppler waveform image UD generated in Step S12 is executed such that the Doppler data is accurately acquired by the Doppler processing unit 7. In general, as illustrated in FIG. 15, since the Doppler waveform WD is periodically changed according to the heartbeat, the adjustment of the Doppler waveform WD is executed from a time point at which a start position and an end position of a heartbeat cycle are detected, for example. The adjustment of the Doppler waveform WD includes adjustment of the lateral axis, that is, the baseline position of the graph of the Doppler waveform WD, and adjustment of the scale of the vertical axis of the Doppler waveform WD. In the adjustment of the Doppler waveform WD, not only the display of the Doppler waveform WD in the display device 9 is adjusted, but also the repetition frequency of the ultrasonic pulses transmitted into the subject from the transducer array 2 of the ultrasound probe 21 is adjusted by the transmission circuit 3 being controlled by the device control unit 15. In this manner, for example, the Doppler waveform WD is adjusted such that the maximum value and the minimum value of the Doppler waveform WD are within 70% of the scale on the vertical axis.

Figure 15:
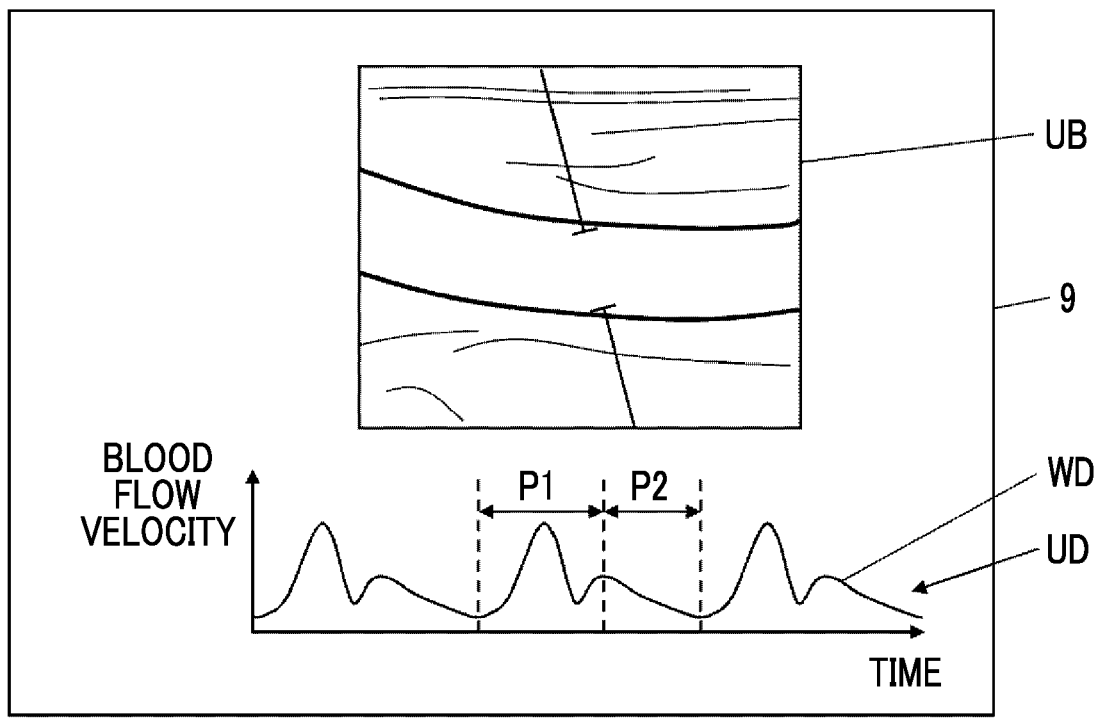
FIG. 15 is a diagram schematically illustrating a B-mode image and a Doppler waveform image displayed on the display device in the first embodiment of the present invention.

In general, since the blood flow velocity in the blood vessel is increased during systole of the heart and is decreased during diastole of the heart, as illustrated in FIG. 15, the amount of change of the Doppler waveform WD in systole P1 is large, and the amount of change of the Doppler waveform WD in diastole P2 is small. Thus, in Step S14, cycle information of the Doppler waveform WD is acquired, and it is determined whether the current time point is the diastole P2 of the heart of the subject on the basis of the acquired cycle information. In a case where it is determined that the current time point is not the diastole P2 of the heart of the subject, the processing of Step S14 is executed again. In a case where it is determined that the current time point is the diastole P2 of the heart of the subject, the processing proceeds to Step S15.

In Step S15, both the B-mode image UB and the Doppler waveform image UD displayed on the display device 9 are frozen and displayed. Here, freezing and displaying the B-mode image UB and the Doppler waveform image UD means that, in a state where the B-mode images UB continuously generated by the B-mode processing unit 6 and the Doppler waveform images UD continuously generated by the Doppler processing unit 7 are displayed on the display device 9, the display of the B-mode image UB and the Doppler waveform image UD is paused and the one paused B-mode image UB and the one paused Doppler waveform image UD are displayed on the display device 9.

In this manner, the Doppler data in the diastole P2 in which the amount of change of the Doppler waveform WD is small can be used for measuring the blood flow rate.

Figure 16:
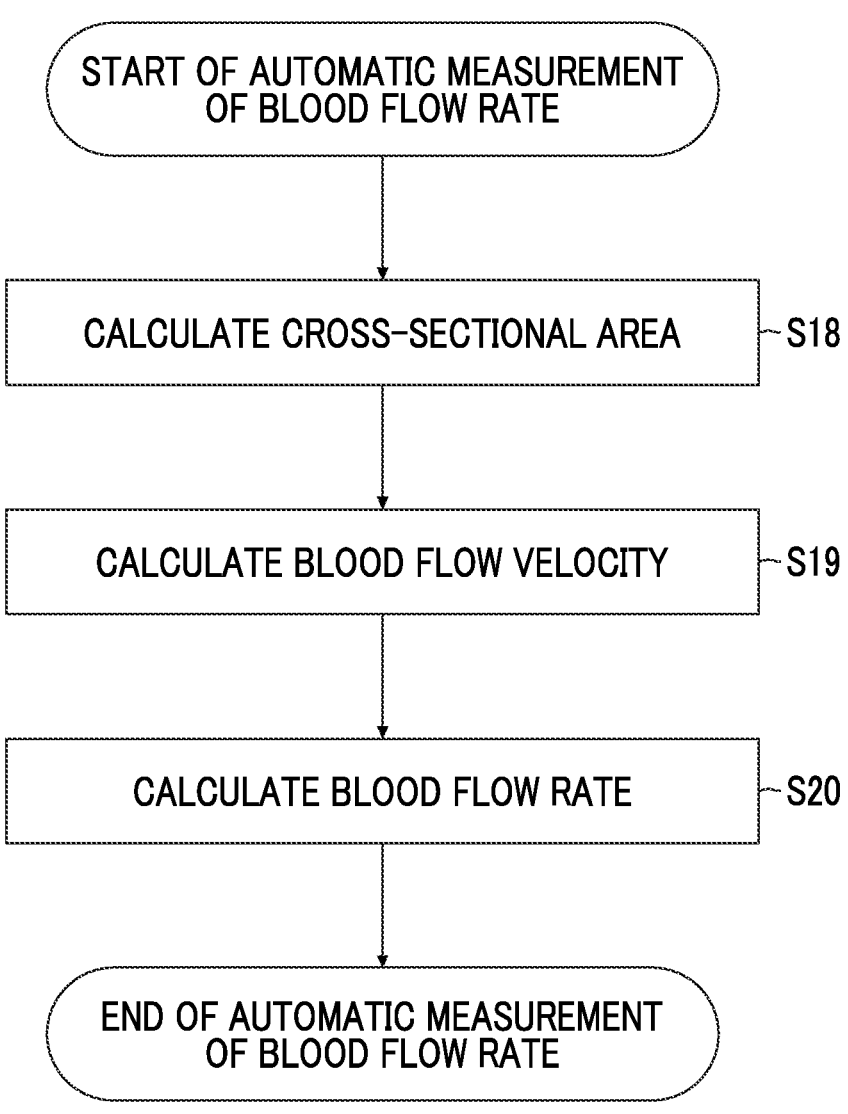
FIG. 16 is a flowchart illustrating an operation of automatically measuring a blood flow rate in the first embodiment of the present invention.

In subsequent Step S16, the blood flow rate in the blood vessel region BR is automatically measured. Step S16 will be described using the flowchart illustrated in FIG. 16.

First, in Step S18, the vascular wall detection unit 10 calculates the cross-sectional area of the blood vessel on the basis of the blood vessel diameter calculated in Step S7, assuming that the blood vessel has a circular cross section.

In Step S19, the blood flow velocity calculation unit 13 calculates the blood flow velocity on the basis of the Doppler data acquired by the Doppler processing unit 7 when the B-mode image UB and the Doppler waveform image UD are frozen and displayed in Step S15. In this case, the blood flow velocity calculation unit 13 can calculate an average blood flow velocity in the heartbeat period.

In Step S20, the blood flow rate measurement unit 12 calculates the blood flow rate representing the volume of the blood flowing in the blood vessel per unit time on the basis of the cross-sectional area of the blood vessel calculated in Step S18 and the blood flow velocity calculated in Step S19.

In this manner, automatic measurement of the blood flow rate in Step S16 is completed.

Figures 17, 18:
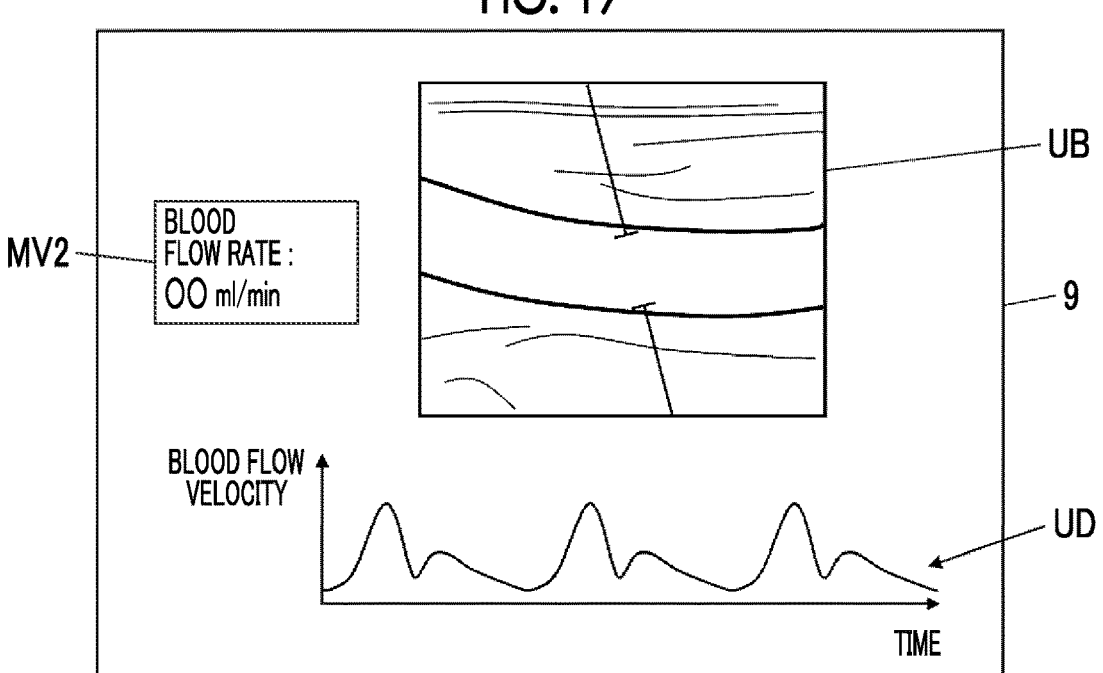
FIG. 17 is a diagram schematically illustrating the B-mode image, the Doppler waveform image, and the measurement value of the blood flow rate displayed on the display device in the first embodiment of the present invention.
FIG. 18 is a diagram schematically illustrating a method of detecting a vascular wall in a modification example of the first embodiment of the present invention.

In Step S17, the measurement result of the blood flow rate obtained in Step S16 is displayed on the display device 9. For example, as illustrated in FIG. 17, a measurement value MV2 of the blood flow rate is displayed on the display device 9 together with the B-mode image UB and the Doppler waveform image UD.

In this manner, in a case where the measurement value MV2 of the blood flow rate is displayed on the display device 9, the operation of the ultrasound diagnostic apparatus 1 is ended.

As described above, with the ultrasound diagnostic apparatus 1 according to the first embodiment of the present invention, in the B-mode images UB of the plurality of frames, with the time point at which the amount of change of the long-axis image of the blood vessel recognized by the vascular wall detection unit 10 is equal to or less than a fixed value as the start trigger, the blood flow rate is automatically measured, and the measurement result of the blood flow rate is displayed on the display device 9 so that the blood flow rate can be easily measured.

Although not illustrated, for example, even in a case where both hands of the user are not empty, such as in a case where the display device 9 is configured by a small portable display and the user holds the display device 9 in one hand and the ultrasound probe 21 in the other hand, with the ultrasound diagnostic apparatus 1 according to the first embodiment of the present invention, it is not necessary for the user to perform an operation through the input device 16 or the like, and therefore the blood flow rate can be easily measured.

In Step S2 in the flowchart illustrated in FIG. 14, the time point at which the amount of change of the long-axis image of the blood vessel is equal to or less than a fixed value is used as the start trigger for the operation of measuring the blood flow rate in Step S3 and subsequent steps, but the start trigger is not limited thereto.

Here, in general, in order to easily find the position of the blood vessel as an imaging target, a procedure is known in which first, the short-axis image of the blood vessel representing the cross section of the blood vessel along a direction orthogonal to the traveling direction of the blood vessel is captured, and the long-axis image of the blood vessel is captured by rotating the direction of the ultrasound probe 21 such that a tomographic plane orthogonal to the tomographic plane of the short-axis image of the blood vessel is imaged. Therefore, for example, with the fact that the blood vessel imaged in the B-mode image UB generated by the B-mode processing unit 6 is changed from the short-axis image to the long-axis image as the start trigger, the blood flow rate can be automatically measured.

Although not illustrated, the ultrasound diagnostic apparatus 1 can comprise a button for giving the start trigger, for example. In this case, the operation of measuring the blood flow rate in Step S3 and subsequent steps is started by the user pressing the button. For example, in a case where the input device 16 is configured by a keyboard, the button for giving the start trigger can be assigned to an appropriate key. For example, in a case where the input device 16 is configured by a touch panel disposed on the display device 9, the button for giving the start trigger can be displayed on the display device 9 such that the button is operated via the touch panel. The button for giving the start trigger may be a foot switch, a mechanical switch, or the like different from the input device 16.

In each of Step S6 and Step S11, the processing proceeds to the next step with the fact that the positions of the detection point markers M1 and M2 are stable as the trigger, but the trigger in Step S6 and Step S11 is not limited thereto. For example, the processing can proceed to Step S7 with the fact that a fixed time such as two seconds has elapsed from the time point at which the detection point markers M1 and M2 are displayed on the display device 9 in Step S5 as the trigger. Similarly, the processing can proceed to Step S12 with the fact that a fixed time such as two seconds has elapsed from the time point at which the operation of setting the Doppler gate DG in Step S10 is completed as the trigger.

Further, for example, Step S6 and Step S11 can be omitted. In this case, the calculation of the blood vessel diameter in Step S7 is performed with the fact that the detection point markers M1 and M2 are disposed on the B-mode image UB in Step S5 as the trigger. Further, the Doppler waveform image UD is generated in Step S12 with the fact that the Doppler gate DG is disposed on the B-mode image UB in Step S10 as the trigger.

The Doppler waveform image UD is generated in Step S12, and the generated Doppler waveform image UD is displayed on the display device 9, but in a case where data of the Doppler waveform WD is acquired, the Doppler waveform image UD may not necessarily be displayed on the display device 9. In this manner, even in a case where the Doppler waveform image UD is not displayed on the display device 9, similar to the case where the Doppler waveform image UD is displayed on the display device 9, the blood flow rate is measured in Step S16 on the basis of the data of the Doppler waveform WD acquired in Step S13 and the blood vessel diameter calculated in Step S7. In a case where the Doppler waveform image UD is not displayed on the display device 9, instead of the Doppler waveform image UD being frozen and displayed on the display device 9 in Step S15, the acquisition of the data of the Doppler waveform WD may be simply stopped.

The example has been described in which in Step S13, the adjustment of the Doppler waveform WD is executed from the time point at which the start position and the end position of the heartbeat cycle in the Doppler waveform WD are detected, but the adjustment of the Doppler waveform WD in Step S13 may be executed with the fact that a fixed time such as two seconds has elapsed from the time point at which the generation of the Doppler waveform image UD in Step S12 is started as the trigger, for example.

In the adjustment of the Doppler waveform WD, in addition to the adjustment of the baseline position and the adjustment of the scale of the vertical axis of the Doppler waveform WD, the position of the Doppler gate DG may be adjusted again such that the maximum value and the minimum value of the Doppler waveform WD are within 70% of the scale on the vertical axis.

Further, for example, Step S13 can be omitted. However, since the accuracy of the blood flow velocity calculated by the blood flow velocity calculation unit 13 can be improved and the accuracy of the blood flow rate measured by the blood flow rate measurement unit 12 can be improved by the adjustment of the Doppler waveform WD, it is preferable to execute Step S13.

In Step S14, the processing proceeds to Step S15 with the fact that the current time point is the diastole P2 of the heart of the subject as the trigger, but the trigger of Step S14 is not limited thereto.

For example, instead of determining whether the current time point is the diastole P2, it may be determined whether the current time point is the systole P1. In this case, in a case where it is determined that the current time point is not the systole P1, it is determined again whether the current time point is the systole P1, and in a case where it is determined that the current time point is the systole P1, the processing proceeds to Step S15. However, since the amount of change of the Doppler waveform WD in the diastole P2 is smaller than that in the systole P1, it is preferable that the processing proceeds to Step S15 with the fact that the current time point is the diastole P2 as the trigger rather than the processing proceeding to Step S15 with the fact that the current time point is the systole P1 as the trigger.

For example, instead of Step S14 being executed, the processing can proceed to Step S15 with the fact that a fixed time such as two seconds has elapsed from the time point at which the operation of adjusting the Doppler waveform WD in Step S13 is completed as the trigger.

For example, instead of Step S14 being executed, the processing can proceed to Step S15 with the fact that the time point at which the start positions and the end positions of a plurality of heartbeat cycles such as two cycles or three cycles in the Doppler waveform WD are detected as the trigger.

In a case where the B-mode image UB and the Doppler waveform image UD are frozen and displayed on the display device 9 in Step S15, the Doppler waveform image UD can be scrolled back and displayed such that the end position of the diastole P2 or the end position of the systole P1 in the Doppler waveform WD is aligned with, for example, the right end portion of the Doppler waveform image UD. In this manner, the position of the Doppler waveform WD displayed on the display device 9 is changed after the B-mode image UB and the Doppler waveform image UD are frozen and displayed, so that the time phase of the B-mode image UB displayed on the display device 9 can be aligned with the diastole P2 or the systole P1.

The Doppler steer angle is set in Step S9 after the B-mode steer angle is set in Step S8, and the Doppler gate DG is set in Step S10 after the Doppler steer angle is set, but the order in which Step S8 to Step S10 are executed is not particularly limited, and can be switched. For example, after the B-mode steer angle is set in Step S8, the setting of the Doppler steer angle of Step S9 and the setting of the Doppler gate DG of Step S10 can be executed in parallel. Further, for example, the processing of Step S8 to Step S10 can be executed in the order of the setting of the Doppler steer angle of Step S9, the setting of the Doppler gate DG of Step S10, and the setting of the B-mode steer angle of Step S8.

In Step S9, the vascular wall detection unit 10 sets the Doppler steer angle such that the angle correction value for the blood vessel traveling angle BA is within 60 degrees, but the blood vessel traveling angle BA can be set as the angle correction value of the Doppler steer angle. In this case, there is a possibility that the angle correction value of the Doppler steer angle exceeds 60 degrees, but in a case where the angle correction value of the Doppler steer angle exceeds 60 degrees, information representing that the angle correction value exceeds 60 degrees can be displayed on the display device 9. For example, the user checks the information representing that the angle correction value exceeds 60 degrees, and adjusts the inclination or the like of the ultrasound probe 21 in contact with the subject, so that automatic measurement of the blood flow velocity by the ultrasound diagnostic apparatus 1 can be performed again.

After the Doppler gate DG is set in Step S10, the blood vessel region BR including the Doppler gate DG in the B-mode image UB is enlarged and displayed on the display device 9. Therefore, the blood vessel region BR on the enlarged B-mode image UB can be clearly checked. In this case, the blood vessel diameter is measured on the basis of the enlarged B-mode image UB. For example, because of the resolution of the B-mode image UB, the position of the vascular wall can be detected more accurately by detecting the vascular wall on the basis of the enlarged B-mode image UB than by detecting the vascular wall on the B-mode image UB before the enlargement, and therefore, the measurement accuracy of the blood flow rate can be improved by measuring the blood vessel diameter on the basis of the enlarged B-mode image UB.

The vascular wall detection unit 10 detects the vascular wall by performing the image analysis on the entire B-mode image UB and setting the search line SL at the position where the brightness change in the vertical direction is the largest in the B-mode image UB, but the method of setting the search line SL is not limited thereto.

For example, the vascular wall detection unit 10 can detect the vascular wall by setting the search line SL such that the search line SL passes through a fixed position such as the center of the B-mode image UB.

For example, as illustrated in FIG. 18, the vascular wall detection unit 10 can recognize the vascular wall by performing the image analysis on a fixed region R1 in the B-mode image UB, and set the search line SL at the position where the brightness change is the largest in the recognized region. In the example illustrated in FIG. 18, the region R1 has a rectangular shape, but the shape of the region R1 is not particularly limited as long as the shape is a closed shape, and may be a polygonal shape, a circular shape, or the like. In this manner, by recognizing the vascular wall in the fixed region R1 and setting the search line SL, the burden on the ultrasound diagnostic apparatus 1 can be reduced as compared with the case of performing the image analysis on the entire B-mode image UB, and it is possible to set the search line SL and detect the vascular wall in a shorter time.

Although not illustrated, the ultrasound diagnostic apparatus 1 comprises a guide unit that guides the user, and the guide unit can cause the display device 9 to display a message to align the blood vessel region BR with the region R1. In this manner, the accuracy with which the vascular wall detection unit 10 recognizes the vascular wall can be improved, and thus the search line SL can be set at a more appropriate position. Therefore, the blood vessel diameter and the cross-sectional area of the blood vessel can be accurately obtained, and the measurement accuracy of the blood flow rate can be improved.

As illustrated in FIGS. 6 and 7, the vascular wall detection unit 10 causes the display device 9 to display the measurement value MV1 of the blood vessel diameter, but the measurement value MV1 of the blood vessel diameter may not necessarily be displayed on the display device 9. However, in a case where the measurement value MV1 of the blood vessel diameter is displayed on the display device 9, it is possible for the user to easily recognize the measurement value MV1 of the blood vessel diameter, which is useful.

In general, it is known that the blood vessel diameter is periodically changed between the minimum diameter and the maximum diameter according to the heartbeat. Thus, although not illustrated, the vascular wall detection unit 10 can cause the display device 9 to display a graph indicating the time change of the measured blood vessel diameter by superimposing the graph on the B-mode image UB. In this manner, it is possible for the user to easily grasp the time change of the blood vessel diameter.

The information on the time change of the blood vessel diameter is acquired so that the minimum diameter and the maximum diameter of the blood vessel are easily measured. For example, the minimum diameter and the maximum diameter of the blood vessel are measured on the basis of the information on the time change of the blood vessel diameter, and the ultrasound diagnostic apparatus 1 can comprise an elastic index calculation unit (not illustrated) that calculates an elastic index representing the elasticity of the blood vessel on the basis of the measured minimum diameter and maximum diameter. The elastic index calculation unit can calculate the difference between the maximum diameter and the minimum diameter of the blood vessel as the elastic index, for example. Further, the elastic index calculation unit can also calculate a normalized value as the elastic index by dividing the difference between the maximum diameter and the minimum diameter of the blood vessel by the minimum diameter of the blood vessel.

By measuring a blood pressure Q1 of the subject at the time point at which the diameter of the blood vessel is the minimum and a blood pressure Q2 of the subject at the time point at which the diameter of the blood vessel is the maximum using a blood pressure manometer (not illustrated), the elastic index calculation unit can calculate a stiffness parameter $X=\{Log(Q2/Q1)\}/\{(D2/D1)-1\}$ disclosed in JP5384919B as the elastic index using the blood pressures Q1 and Q2, the minimum diameter D1 of the blood vessel, and the maximum diameter D2 of the blood vessel.

The vascular wall detection unit 10 searches for both the anterior vascular wall W1 and the posterior vascular wall W2 in a case of estimating the gradient of the blood vessel, but can estimate a virtual blood vessel gradient line BL representing the gradient of the blood vessel by searching for any one of the anterior vascular wall W1 or the posterior vascular wall W2.

Second Embodiment

In Step S12 in the operation of the ultrasound diagnostic apparatus 1 of the first embodiment, the B-mode image UB and the Doppler waveform image UD are generated in parallel, but the generation of the B-mode image UB can be temporarily stopped, and only the Doppler waveform image UD can be generated.

Figure 19:
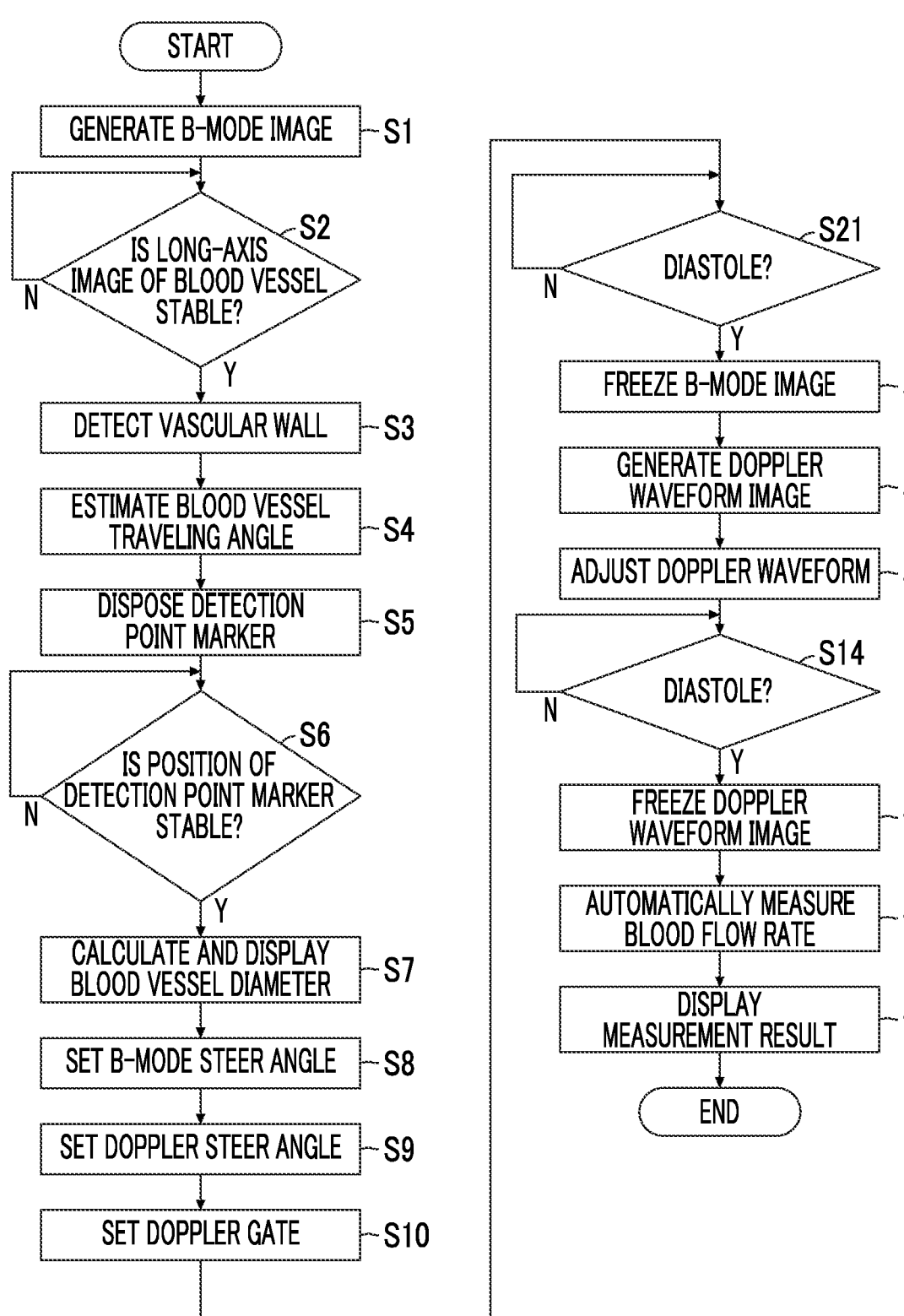
FIG. 19 is a flowchart illustrating an operation of an ultrasound diagnostic apparatus according to a second embodiment of the present invention.

In the following, the operation of the ultrasound diagnostic apparatus 1 according to a second embodiment will be described in detail using the flowchart illustrated in FIG. 19. The flowchart is obtained by adding Step S21 to Step S23 instead of Step S11 and Step S12, and Step S24 instead of Step S15 to the flowchart of the first embodiment illustrated in FIG. 14.

First, in Step S1, the B-mode processing unit 6 generates the B-mode image UB in which at least the blood vessel is imaged, and causes the display device 9 to display the generated B-mode image UB. In the subsequent steps, it is assumed that the B-mode images UB are continuously generated by the B-mode processing unit 6.

In Step S2, the vascular wall detection unit 10 performs the image analysis on the B-mode images UB of a plurality of frames continuously generated in Step S1, and recognizes the long-axis image of the blood vessel in the B-mode image UB. In Step S2, it is determined whether the position of the long-axis image of the blood vessel recognized by the vascular wall detection unit 10 is stable for each of the B-mode images UB continuously generated in Step S1. In a case where it is determined in Step S2 that the position of the long-axis image of the blood vessel is not stable, the processing of Step S2 is performed again so that the long-axis image of the blood vessel in newly generated B-mode images UB of a plurality of frames is recognized, and it is determined whether the position of the long-axis image of the blood vessel is stable. In a case where it is determined in Step S2 that the position of the long-axis image of the blood vessel is stable, the processing proceeds to Step S3.

In this manner, with the time point at which the amount of change of the long-axis image of the blood vessel in the B-mode image UB is equal to or less than a fixed value as the start trigger, the operation of automatically measuring the blood flow rate is performed in Step S3 and subsequent steps.

As illustrated in FIG. 4, in Step S3, the vascular wall detection unit 10 detects the positions of the two points X1 and X2 as the position of the anterior vascular wall W1 and the position of the posterior vascular wall W2 of the blood vessel included in the B-mode image UB by analyzing the B-mode image UB generated in Step S1.

In Step S4, the vascular wall detection unit 10 sets the virtual blood vessel gradient line BL representing the gradient of the blood vessel on the B-mode image UB as illustrated in FIG. 5 by analyzing the B-mode image UB, and estimates the blood vessel traveling angle BA as illustrated in FIG. 8 on the basis of the set blood vessel gradient line BL.

In Step S5, as illustrated in FIG. 6, the vascular wall detection unit 10 disposes the detection point markers M1 and M2 at the positions of the two points X1 and X2 detected as the position of the anterior vascular wall W1 and the position of the posterior vascular wall W2 in Step S3, and causes the display device 9 to display the disposed detection point markers M1 and M2.

As illustrated in FIG. 7, the vascular wall detection unit 10 can dispose the detection point markers M1 and M2 at the position of the intersection between the straight line TL orthogonal to the blood vessel gradient line BL estimated in Step S4 and the anterior vascular wall W1, and the position of the intersection between the straight line TL and the posterior vascular wall W2, and cause the display device 9 to display the disposed detection point markers M1 and M2.

In subsequent Step S6, it is determined whether the positions of the detection point markers M1 and M2 disposed on the B-mode image UB in Step S5 are stable for each B-mode image UB generated by the B-mode processing unit 6. In a case where it is determined in Step S6 that the positions of the detection point markers M1 and M2 are not stable, the processing of Step S6 is performed again so that it is determined whether the positions of the detection point markers M1 and M2 in newly generated B-mode images UB of a plurality of frames are stable. In a case where it is determined in Step S6 that the positions of the detection point markers M1 and M2 are stable, the processing proceeds to Step S7.

In Step S7, the vascular wall detection unit 10 measures the distance between the two disposed detection point markers M1 and M2 as the blood vessel diameter, and causes the display device 9 to display the measurement value MV1 of the blood vessel diameter which is measured, as illustrated in FIG. 6 or FIG. 7, for example.

Also in the subsequent steps, the processing of Step S3 to Step S7 is executed each time the B-mode image UB is generated by the B-mode processing unit 6.

In subsequent Step S8, the vascular wall detection unit 10 sets the B-mode steer angle representing the inclination angle of the scan line when the B-mode image UB is generated by the B-mode processing unit 6, by using the blood vessel traveling angle BA estimated in Step S4.

In Step S9, the vascular wall detection unit 10 sets the Doppler steer angle representing the inclination angle of the scan line when the Doppler data is acquired by the Doppler processing unit 7, by using the blood vessel traveling angle BA estimated in Step S4.

In Step S10, as illustrated in FIG. 12, the gate setting unit 11 sets the Doppler gate DG having a size and a center position decided on the basis of the coordinates of the anterior vascular wall W1 and the coordinates of the posterior vascular wall W2 detected in Step S3, in the blood vessel region BR on the B-mode image UB. Further, the gate setting unit 11 causes the display device 9 to display the set Doppler gate DG on the B-mode image UB in a superimposed manner.

Figure 20:
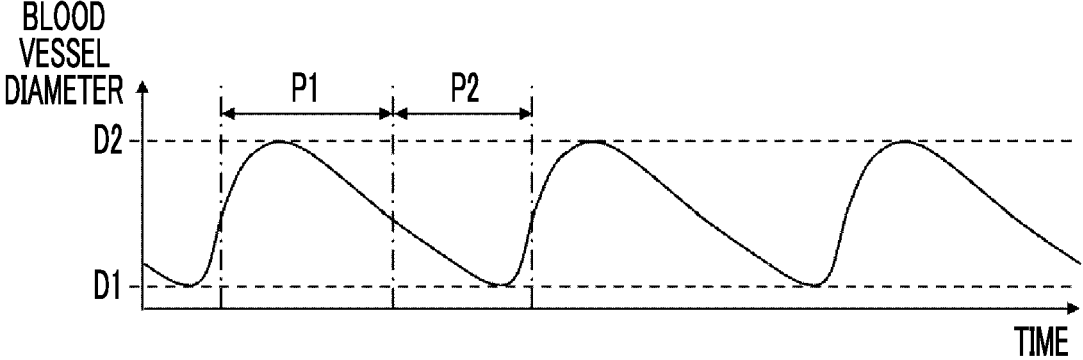
FIG. 20 is a diagram schematically illustrating a time change of the blood vessel diameter in the second embodiment of the present invention.

In a case where the processing of Step S10 is completed, in Step S21, it is determined whether the current time point is the diastole P2 of the heart of the subject on the basis of the blood vessel diameter measured in Step S7. Here, as illustrated in FIG. 20, in general, the blood vessel diameter is periodically changed between the minimum diameter D1 and the maximum diameter D2 according to the heartbeat, the systole P1 of the heart has the maximum diameter D2, and the diastole P2 of the heart has the minimum diameter D1. Therefore, for example, the minimum diameter D1 of the blood vessel is measured, so that it is determined that the current time point is the diastole P2 of the heart of the subject. In a case where it is determined that the current time point is not the diastole P2 of the heart of the subject, the processing of Step S21 is executed again. In a case where it is determined that the current time point is the diastole P2 of the heart of the subject, the processing proceeds to Step S22.

In Step S22, the B-mode image UB displayed on the display device 9 is frozen and displayed.

In subsequent Step S23, the Doppler processing unit 7 starts to continuously generate the Doppler waveform images UD, and causes the display device 9 to display the generated Doppler waveform images UD. In this manner, the Doppler waveform image UD is displayed on the display device 9 in a state where the B-mode image UB is frozen and displayed on the display device 9.

In this manner, in a case where the Doppler waveform image UD is displayed on the display device 9, the adjustment of the Doppler waveform WD in the Doppler waveform image UD generated in Step S23 is executed in Step S13.

In Step S14, the cycle information of the Doppler waveform WD is acquired, and it is determined whether the current time point is the diastole P2 of the heart of the subject on the basis of the acquired cycle information. In a case where it is determined that the current time point is not the diastole P2 of the heart of the subject, the processing of Step S14 is executed again. In a case where it is determined that the current time point is the diastole P2 of the heart of the subject, the processing proceeds to Step S24.

In Step S24, the Doppler waveform image UD displayed on the display device 9 is frozen and displayed. In this manner, the B-mode image UB and the Doppler waveform image UD in the diastole P2 are frozen and displayed on the display device 9, and the blood vessel diameter measured from the B-mode image UB in the diastole P2 and the Doppler data in the diastole P2 in which the amount of change of the Doppler waveform WD is small can be used for the measurement of the blood flow rate.

In subsequent Step S16, the blood flow rate in the blood vessel region BR is automatically measured, and in Step S17, as illustrated in FIG. 17, the measurement value MV2 of the blood flow rate is displayed on the display device 9 together with the B-mode image UB and the Doppler waveform image UD.

In this manner, in a case where the measurement value MV2 of the blood flow rate is displayed on the display device 9, the operation of the ultrasound diagnostic apparatus 1 is ended.

As described above, with the ultrasound diagnostic apparatus 1 according to the second embodiment of the present invention, even in a case where the generation of the B-mode image UB is temporarily stopped and only the Doppler waveform image UD is generated, similar to the case where both the B-mode image UB and the Doppler waveform image UD are simultaneously generated in the first embodiment, with the time point at which the amount of change of the long-axis image of the blood vessel recognized by the vascular wall detection unit 10 is equal to or less than a fixed value as the start trigger, the blood flow rate is automatically measured, and the measurement result of the blood flow rate is displayed on the display device 9 so that the blood flow rate can be easily measured.

Although not illustrated, for example, even in a case where both hands of the user are not empty, such as in a case where the display device 9 is configured by a small portable display and the user holds the display device 9 in one hand and the ultrasound probe 21 in the other hand, with the ultrasound diagnostic apparatus 1 according to the second embodiment of the present invention, it is not necessary for the user to perform an operation through the input device 16 or the like, and therefore the blood flow rate can be easily measured.

In Step S21, the processing proceeds to Step S22 with the fact that the current time point is the diastole P2 of the heart of the subject as the trigger, but the trigger of Step S21 is not limited thereto.

For example, instead of determining whether the current time point is the diastole P2, it may be determined whether the current time point is the systole P1. In this case, in a case where it is determined that the current time point is not the systole P1, it is determined again whether the current time point is the systole P1, and in a case where it is determined that the current time point is the systole P1, the processing proceeds to Step S22. However, since the amount of change of the Doppler waveform WD in the diastole P2 is smaller than that in the systole P1, it is preferable that the processing proceeds to Step S22 with the fact that the current time point is the diastole P2 as the trigger rather than the processing proceeding to Step S22 with the fact that the current time point is the systole P1 as the trigger.

For example, similar to Step S2 and Step S6, the processing proceeds to Step S22 with the fact that the positions of the detection point markers M1 and M2 are stable as the trigger.

For example, the processing can proceed to Step S22 with the fact that a fixed time such as two seconds has elapsed from the time point at which the setting of the Doppler gate DG in Step S10 is completed as the trigger.

Further, for example, Step S21 can be omitted. In this case, the B-mode image UB is frozen and displayed on the display device 9 in Step S22 with the fact that the Doppler gate DG is set on the B-mode image UB in Step S10 as the trigger.

The Doppler waveform image UD is generated in Step S23, and the generated Doppler waveform image UD is displayed on the display device 9, but similar to Step S12 in the first embodiment, in a case where data of the Doppler waveform WD is acquired, the Doppler waveform image UD may not necessarily be displayed on the display device 9.

Third Embodiment

In the first embodiment, the example has been described in which the time point at which the amount of change of the long-axis image of the blood vessel in the B-mode image UB is equal to or less than a fixed value is used as the start trigger for the operation of automatically measuring the blood flow rate, but the voice of the user can be used as the start trigger.

Figure 21:
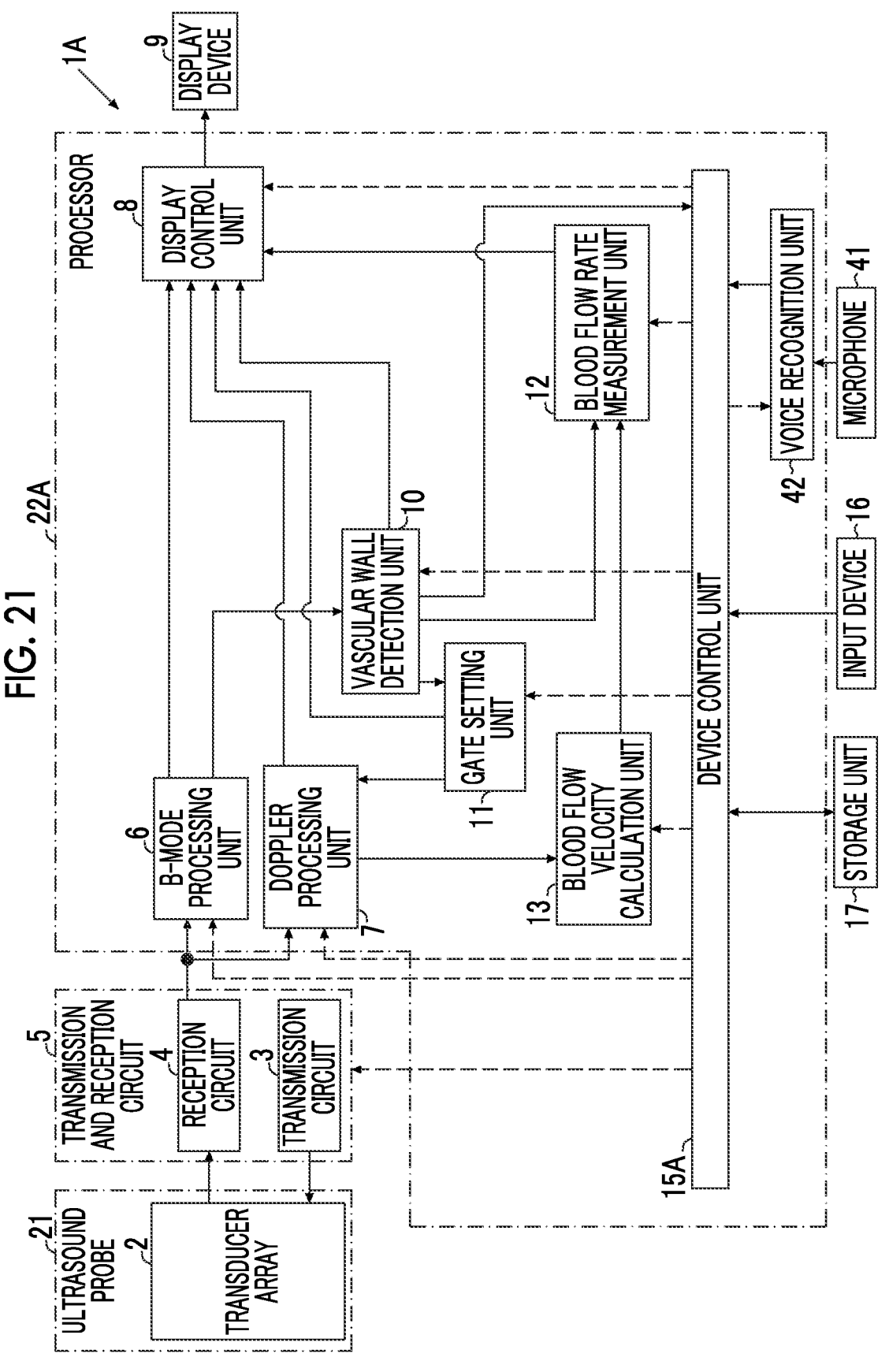
FIG. 21 is a block diagram illustrating a configuration of an ultrasound diagnostic apparatus according to a third embodiment of the present invention.

FIG. 21 illustrates a configuration of an ultrasound diagnostic apparatus 1A according to a third embodiment. The ultrasound diagnostic apparatus 1A according to the third embodiment is obtained by comprising a device control unit 15A instead of the device control unit 15 and adding a microphone 41 and a voice recognition unit 42 to the ultrasound diagnostic apparatus 1 of the first embodiment illustrated in FIG. 1.

In the ultrasound diagnostic apparatus 1A, the voice recognition unit 42 is connected to the microphone 41, and the device control unit 15A is connected to the voice recognition unit 42. Further, the B-mode processing unit 6, the Doppler processing unit 7, the display control unit 8, the vascular wall detection unit 10, the gate setting unit 11, the blood flow rate measurement unit 12, the blood flow velocity calculation unit 13, the device control unit 15A, and the voice recognition unit 42 constitute a processor 22A for the ultrasound diagnostic apparatus 1A.

The voice recognition unit 42 recognizes the user's voice input through the microphone 41, and gives the start trigger for starting the measurement of the blood flow rate to the device control unit 15A on the basis of the recognized user's voice. For example, the voice recognition unit 42 determines whether the voice input through the microphone 41 means to start the measurement of the blood flow rate by extracting a fixed keyword relating to the measurement of the blood flow rate from the user's voice, and in a case where it is determined that the user's voice means to start the measurement of the blood flow rate, the voice recognition unit 42 can give the start trigger relating to the measurement of the blood flow rate to the device control unit 15A.

In a case where the start trigger is given from the voice recognition unit 42, the device control unit 15A controls each unit of the ultrasound diagnostic apparatus 1A to start automatically measuring the blood flow rate.

In this manner, with the ultrasound diagnostic apparatus 1A according to the third embodiment, since only by instructing to start measuring the blood flow rate by the user's voice, the start trigger relating to the measurement of the blood flow rate is given on the basis of the user's voice, and the blood flow rate is automatically measured so that the measurement result of the blood flow rate is displayed on the display device 9, it is possible to easily measure the blood flow rate even in a case where both hands of the user are not empty.

Fourth Embodiment

The ultrasound diagnostic apparatus 1 of the first embodiment has the configuration in which the display device 9, the input device 16, and the ultrasound probe 21 are directly connected to the processor 22, but, for example, the display device 9, the input device 16, the ultrasound probe 21, and the processor 22 can be indirectly connected to each other via the network.

Figure 22:
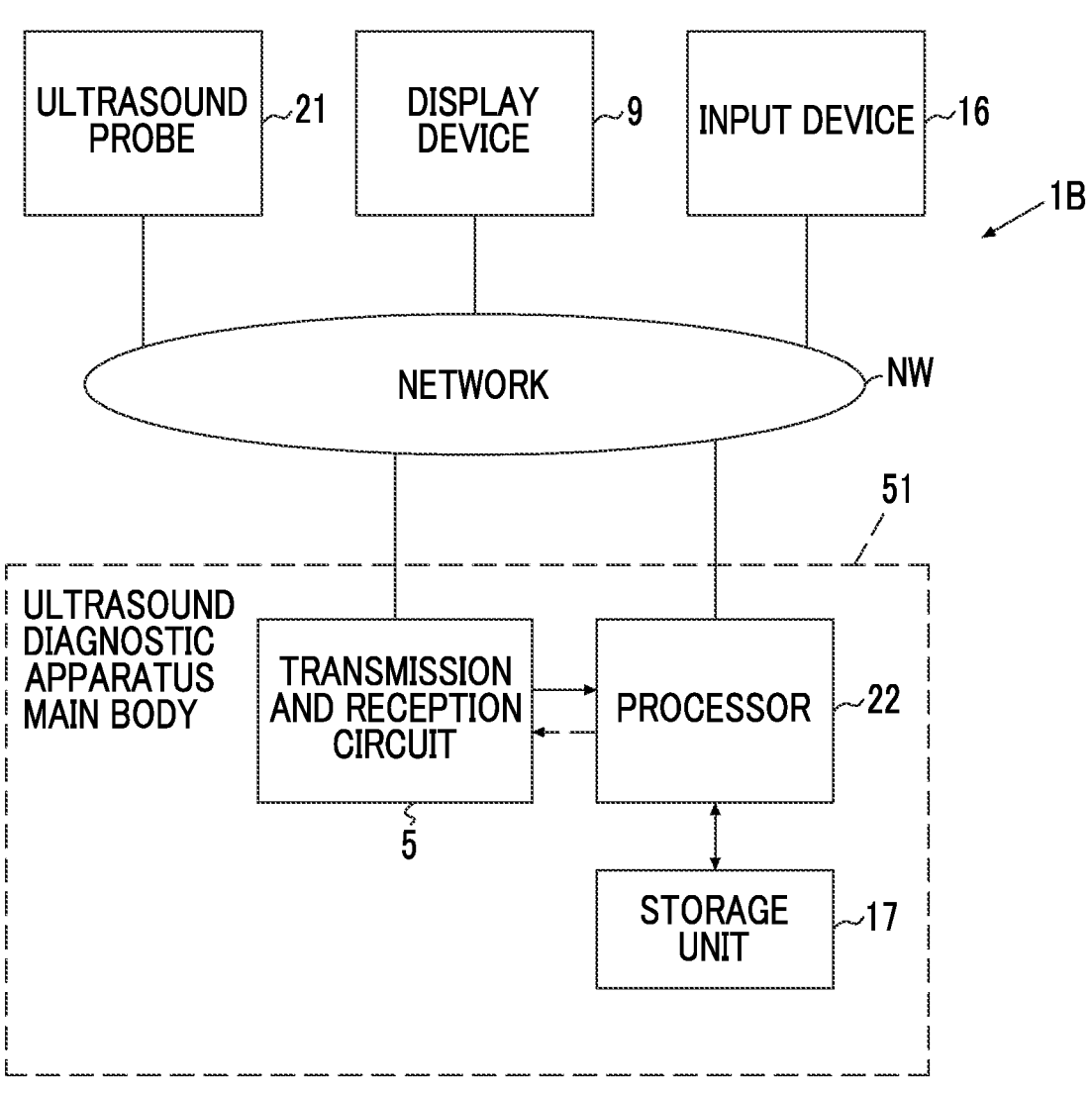
FIG. 22 is a block diagram illustrating a configuration of an ultrasound diagnostic apparatus according to a fourth embodiment of the present invention.

As illustrated in FIG. 22, in an ultrasound diagnostic apparatus 1B in a fourth embodiment, the display device 9, the input device 16, and the ultrasound probe 21 are connected to an ultrasound diagnostic apparatus main body 51 via a network NW. The ultrasound diagnostic apparatus main body 51 is obtained by excluding the display device 9, the input device 16, and the ultrasound probe 21 in the ultrasound diagnostic apparatus 1 of the first embodiment illustrated in FIG. 1, and is constituted by the transmission and reception circuit 5, the storage unit 17, and the processor 22.

Even in a case where the ultrasound diagnostic apparatus 1B is configured as described above, similar to the ultrasound diagnostic apparatus 1 of the first embodiment, in the B-mode images UB of the plurality of frames, with the time point at which the amount of change of the long-axis image of the blood vessel recognized by the vascular wall detection unit 10 is equal to or less than a fixed value as the start trigger, the blood flow rate is automatically measured, and the measurement result of the blood flow rate is displayed on the display device 9 so that the blood flow rate can be easily measured.

Further, since the display device 9, the input device 16, and the ultrasound probe 21 are connected to the ultrasound diagnostic apparatus main body 51 via the network NW, the ultrasound diagnostic apparatus main body 51 can be used as a so-called remote server. Thereby, for example, since the user can perform a diagnosis of the subject by preparing the display device 9, the input device 16, and the ultrasound probe 21 at the user's hand, it is possible to improve the convenience in a case of the ultrasound diagnosis.

Further, in a case where a portable thin computer, for example, a so-called tablet, is used as the display device 9 and the input device 16, it is possible for the user to more easily perform the ultrasound diagnosis of the subject, and it is possible to further improve the convenience in a case of the ultrasound diagnosis.

The display device 9, the input device 16, and the ultrasound probe 21 are connected to the ultrasound diagnostic apparatus main body 51 via the network NW, but in this case, the display device 9, the input device 16, and the ultrasound probe 21 may be connected to the network NW in a wired manner or in a wireless manner.

Further, it is described that the form of the fourth embodiment is applied to the first embodiment, but the form of the fourth embodiment can be similarly applied to the second embodiment and the third embodiment.

EXPLANATION OF REFERENCES

1, 1A, 1B: ultrasound diagnostic apparatus
2: transducer array
3: transmission circuit
4: reception circuit
5: transmission and reception circuit
6: B-mode processing unit
7: Doppler processing unit
8: display control unit
9: display device
10: vascular wall detection unit
11: gate setting unit
12: blood flow rate measurement unit
13: blood flow velocity calculation unit
15, 15A: device control unit
16: input device
17: storage unit
21: ultrasound probe
22, 22A: processor
23: amplification unit
24: AD conversion unit
25: beam former
26: signal processing unit
27: DSC
28: image processing unit
29: quadrature detection unit
30: high-pass filter
31: fast Fourier transformer
32: Doppler waveform image generation unit
33: data memory
41: microphone
42: voice recognition unit
51: ultrasound diagnostic apparatus main body
A1, B1, B2, H: angle
BA: blood vessel traveling angle
BR: blood vessel region
BL: blood vessel gradient line
C: midpoint
E: estimation error
D1: minimum diameter
D2: maximum diameter
DG: Doppler gate
J, L1, TL: straight line
K1: distance
LG: gate width
M2: detection point marker
MV1: measurement value
MV2: measurement value
NW: network
P1: systole
P2: diastole
R1: region
SL: search line
UB: B-mode image
UD: Doppler waveform image
W1: anterior vascular wall
W2: posterior vascular wall
WD: Doppler waveform
X1, X2: point

What is claimed is:

1. An ultrasound diagnostic apparatus comprising:

a display device;

a transducer configured to obtain a reception signal by transmitting and receiving ultrasonic waves to and from a subject and converting the received ultrasonic waves to the reception signal; and a processor configured to sequentially generate a plurality of B-mode images in which at least a blood vessel is imaged based on the reception signal obtained by the transducer, where the plurality of B-mode images represent a longitudinal cross section along a traveling direction of the blood vessel, calculate a change amount of a position of the blood vessel within a predetermined time on the plurality of B-mode images, and upon determining that the position of the blood vessel is stable due to the change amount being equal to or less than a fixed value, automatically perform a process including:

detecting a vascular wall by analyzing at least one of the plurality of B-mode images;

setting a Doppler gate in the blood vessel on the plurality of B-mode images;

acquiring Doppler data in the Doppler gate;

calculating a blood flow velocity based on the Doppler data; and measuring a blood flow rate based on the vascular wall and the blood flow velocity, wherein the processor is further configured to search for an anterior vascular wall in a shallow direction and search for a posterior vascular wall in a deep direction, at a plurality of positions separated in an orientation direction from a center position decided based on coordinates of the anterior vascular wall and the posterior vascular wall, estimate a blood vessel traveling angle, and set a Doppler steer angle such that an angle correction value for the blood vessel traveling angle is within 60 degrees.

2. The ultrasound diagnostic apparatus according to claim 1, wherein the processor is further configured to calculate a cross-sectional area of the blood vessel based on the detected vascular wall, and measure the blood flow rate by the product of the cross-sectional area and the blood flow velocity.

3. The ultrasound diagnostic apparatus according to claim 1, wherein the processor is further configured to generate a Doppler waveform image based on the Doppler data, and the display device is configured to display both the B-mode image and the Doppler waveform image.

4. The ultrasound diagnostic apparatus according to claim 1, wherein the processor is further configured to generate a Doppler waveform image in parallel with the generation of the B-mode image, and measure the blood flow rate with both the B-mode image and the Doppler waveform image being frozen.

5. The ultrasound diagnostic apparatus according to claim 1, wherein the processor is further configured to acquire the Doppler data in the Doppler gate and generate a Doppler waveform image after the B-mode image is frozen, and measure the blood flow rate with the Doppler waveform image being frozen.

6. The ultrasound diagnostic apparatus according to claim 1, wherein the processor is further configured to set a search line for searching for the vascular wall on the B-mode image, and detect the anterior vascular wall and the posterior vascular wall as the vascular wall based on a brightness profile of the B-mode image on the set search line.

7. The ultrasound diagnostic apparatus according to claim 6, wherein the processor is further configured to set the Doppler gate having a size and a center position decided based on coordinates of the anterior vascular wall and the posterior vascular wall.

8. The ultrasound diagnostic apparatus according to claim 6, wherein the processor is further configured to calculate a cross-sectional area of the blood vessel based on the detected vascular wall, and measure the blood flow rate by the product of the cross-sectional area and the blood flow velocity.

9. The ultrasound diagnostic apparatus according to claim 6, wherein the processor is further configured to set a detection point marker on each of the detected anterior vascular wall and the detected posterior vascular wall, and cause the display device to display the detection point marker.

10. The ultrasound diagnostic apparatus according to claim 9, wherein the processor is further configured to calculate a cross-sectional area of the blood vessel based on the detected vascular wall, and measure the blood flow rate by the product of the cross-sectional area and the blood flow velocity.

11. The ultrasound diagnostic apparatus according to claim 9, wherein the processor is further configured to set the Doppler gate having a size and a center position decided based on coordinates of the anterior vascular wall and the posterior vascular wall.

12. The ultrasound diagnostic apparatus according to claim 11, wherein the processor is further configured to generate the plurality of B-mode images based on a B-mode steer angle set according to a blood vessel traveling angle.

13. A control method of an ultrasound diagnostic apparatus, the control method comprising:

obtaining a reception signal from a transducer configured to transmit and receive ultrasonic waves to and from a subject and convert the received ultrasonic waves to the reception signal;

sequentially generating a plurality of B-mode images in which at least a blood vessel is imaged based on the reception signal obtained by the transducer, where the plurality of B-mode images represent a longitudinal cross section along a traveling direction of the blood vessel;

sequentially displaying each of the plurality of B-mode images;

calculating a change amount of a position of the blood
vessel within a predetermined time on the plurality of
B-mode images; and upon determining that the position of the blood vessel is
stable due to the change amount being equal to or less
than a fixed value, automatically perform a process
including:

detecting a vascular wall by analyzing at least one of
the plurality of B-mode images;

setting a Doppler gate in the blood vessel on the plurality of B-mode images;

acquiring Doppler data in the Doppler gate;

calculating a blood flow velocity based on the Doppler
data; and measuring a blood flow rate based on the detected
vascular wall and the calculated blood flow velocity, wherein the control method further comprises searching for an anterior vascular wall in a shallow
direction and searching for a posterior vascular wall
in a deep direction, at a plurality of positions separated in an orientation direction from a center posi-
tion decided based on coordinates of the anterior
vascular wall and the posterior vascular wall, estimating a blood vessel traveling angle, and setting a Doppler steer angle such that an angle correction value for the blood vessel traveling angle is
within 60 degrees.

* * * * *